(12) United States Patent
Takagi et al.

(10) Patent No.: US 7,186,231 B2
(45) Date of Patent: Mar. 6, 2007

(54) BLOOD COMPONENT COLLECTION METHOD

(75) Inventors: Yoshiki Takagi, Fujinomiya (JP); Shigeyuki Kimura, Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 370 days.

(21) Appl. No.: 10/473,168

(22) PCT Filed: Mar. 19, 2002

(86) PCT No.: PCT/JP02/02625

§ 371 (c)(1),
(2), (4) Date: Sep. 29, 2003

(87) PCT Pub. No.: WO02/078769

PCT Pub. Date: Oct. 10, 2002

(65) Prior Publication Data

US 2004/0112808 A1    Jun. 17, 2004

(30) Foreign Application Priority Data

Mar. 28, 2001 (JP) .............................. 2001-094102

(51) Int. Cl.
*A61M 1/00* (2006.01)
*A61M 1/38* (2006.01)
*B01D 21/26* (2006.01)
*B01D 37/00* (2006.01)
*B04B 9/10* (2006.01)
*B04B 11/00* (2006.01)

(52) U.S. Cl. .................. 604/6.01; 210/97; 210/109; 210/134; 210/143; 210/252; 210/257.1; 210/258; 210/418; 210/782; 210/789; 604/4.01; 604/5.01; 604/6.03; 604/6.04; 604/6.09; 604/6.1; 604/6.11; 604/6.15; 494/36; 494/37

(58) Field of Classification Search .................. 210/97, 210/109, 134, 143, 252, 257.1, 258, 418, 210/420, 435, 781, 782, 789; 604/4.01, 5.01, 604/6.01, 6.03, 6.04, 6.09, 6.1, 6.11, 6.15; 494/37, 43, 60, 36
See application file for complete search history.

(56) References Cited

U.S. PATENT DOCUMENTS 5,637,082 A * 6/1997 Pages et al. ............... 604/6.11

(Continued)

FOREIGN PATENT DOCUMENTS

JP      A 7-265407      10/1995

*Primary Examiner*—John Kim
(74) *Attorney, Agent, or Firm*—Oliff & Berridge, PLC

(57) ABSTRACT

An object is to provide a blood component collection system capable of collecting a desired blood component of high quality. A blood component collection system 1 comprises a centrifugal separator 20 centrifuging blood into a plurality of components, first line 21 for feeding the blood to the centrifugal separator 20, a second line 22 for releasing the blood component from the centrifugal separator 20, a temporary reservoir bag 26' for temporarily reserving the platelet concentrate, a leukoreduction filter 261 for separating and reducing leukocyte from the platelet concentrate, and a platelet collection bag 26 for reserving the platelet concentrate having passed through the leukoreduction filter 261. The blood component collection system 1 is constructed to feed the platelet concentrate in the temporary reservoir bag 26' to the platelet collection bag 26 through the leukoreduction filter 261, and then, feed plasma and collect the platelet remaining in the leukoreduction filter 261 (platelet concentrate from which leukocyte have been reduced) together with the plasma into the platelet collection bag 26.

20 Claims, 8 Drawing Sheets

U.S. PATENT DOCUMENTS 5,690,815 A * 11/1997 Krasnoff et al. .............. 210/97
5,762,791 A * 6/1998 Deniega et al. ........ 210/321.67
5,865,785 A * 2/1999 Bischof .................... 604/6.03
6,752,777 B1 * 6/2004 Takagi et al. .............. 604/6.01
6,945,411 B1 * 9/2005 Bormann et al. ........... 210/491

* cited by examiner

BLOOD COMPONENT COLLECTION METHOD

TECHNICAL FIELD

The present invention relates to a blood component collection system for separating blood into a plurality of components and collecting any of the separated components.

BACKGROUND ART

To collect blood, currently, blood component collection is adopted for the purposes of effectively utilizing blood and alleviating a burden a donor must incur. Namely, the collected blood is separated into components through centrifugation or the like, only a component needed for a patient to be transfused is collected, and the other components are restored to a donor.

In the component collection, for preparing a platelet product, blood collected from a donor is routed to a blood component collection circuit. A centrifugal separator called a centrifugal bowl included in the blood component collection circuit is used to separate the blood into components, that is, plasma, a buffy coat, and red blood cells. Platelets are separated from the buffy coat and collected into a container, whereby a platelet product is prepared. The remaining plasma, white blood cells, and red blood cells are returned to the donor.

However, according to the above method, when a large number of platelets is needed, the number of leukocyte (white blood cells) mixed in a platelet product increases. This leads to an increase in the risk of an attack of fever, alloimmunization, virus infection, or the like.

In efforts to cope with the above problem, proposals have been made of a method according to which collected platelets are passed through a leukoreduction filter (leukocyte removal filter) in order to separate or reduce leukocyte, and the platelets separated from the leukocyte are collected in order to prepare a leukocyte reduced platelet product. In this case, platelets remain in the leukoreduction filter. In order to improve the yield of platelets, the leukoreduction filter is cleansed using a cleanser such as physiological saline or an anticoagulant.

However, according to the above method, the cleanser is mixed in the platelet product. This poses a problem that the quality of the platelet product is degraded.

DISCLOSURE OF INVENTION

An object of the present invention is to provide a blood component collection system capable of collecting a desired blood component of high quality.

To achieve the above object, the present invention provides a blood component collection system comprising: a centrifugal separator including a rotor having a blood reservoir space therein and an inlet and an outlet which communicate with the blood reservoir space, and centrifuging blood introduced through the inlet by rotation of the rotor, into a plurality of components in the blood reservoir space; a first container for temporarily reserving therein a first blood component; a cell separating filter for separating or reducing a predetermined kind of cells from the first blood component; and a second container for reserving the first blood component having passed through the cell separating filter, wherein the blood component collection system further comprises: channel open/close means for opening or closing a channel linking the first container and the cell separating filter; and control means for controlling action of the channel open/close means, the channel open/close means is used to carry the first blood component in the first container to the second container through the cell separating filter, then supply a second blood component, and collect the first blood component, from which the predetermined kind of cells remaining in the cell separating filter have been separated or reduced, together with the second blood component into the second container.

According to another aspect, the present invention provides a blood component collection system comprising: a centrifugal separator including a rotor having a blood reservoir space therein and an inlet and an outlet which communicate with the blood reservoir space, and centrifuging blood introduced through the inlet by rotation of the rotor, into a plurality of components in the blood reservoir space; a first container for temporarily reserving therein a first blood component; a cell separating filter connected to the first container through a feed tube, and used to separate or reduce a predetermined kind of cells from the first blood component fed through the feed tube; and a second container which is connected to the.cell separating filter through a release tube and used for reserving therein the first blood component having passed through the cell separating filter, wherein the blood component collection system further comprises: channel open/close means for opening or closing a channel of the feed tube; and control means for controlling action of the channel open/close means, the channel open/close means is used to carry the first blood component in the first container to the second container through the feed tube, cell separating filter, and release tube in response to a command sent from the control means, thereafter, a second blood component is fed, and the first blood component that remains in the cell separating filter and the channel of the release tube and that has the predetermined cells separated or reduced therefrom is collected together with the second blood component into the second container.

Preferably, in the blood component collection system according to the present invention, a full amount of a blood component to be collected into the second container is adjusted according to a fed amount of the second blood component. Specifically, the fed amount of the second blood component is determined based on a difference between a target full amount of the blood component to be collected into the second container and an amount of the first blood component to be carried to the second container.

More preferably, the blood component collection system according to the present invention further includes a third container for reserving the second blood component, wherein the second blood component is fed from the third container.

Preferably, in the blood component collection system according to the present invention, the second blood component is fed together with the first blood component which remains in the first container, to the cell separating filter.

More preferably, in the blood component collection system according to the present invention, the first blood component is plasma containing platelets, the second blood component is plasma, ant the cell separating filter is a leukoreduction filter.

BEST MODE FOR CARRYING OUT THE INVENTION

Figure 1:
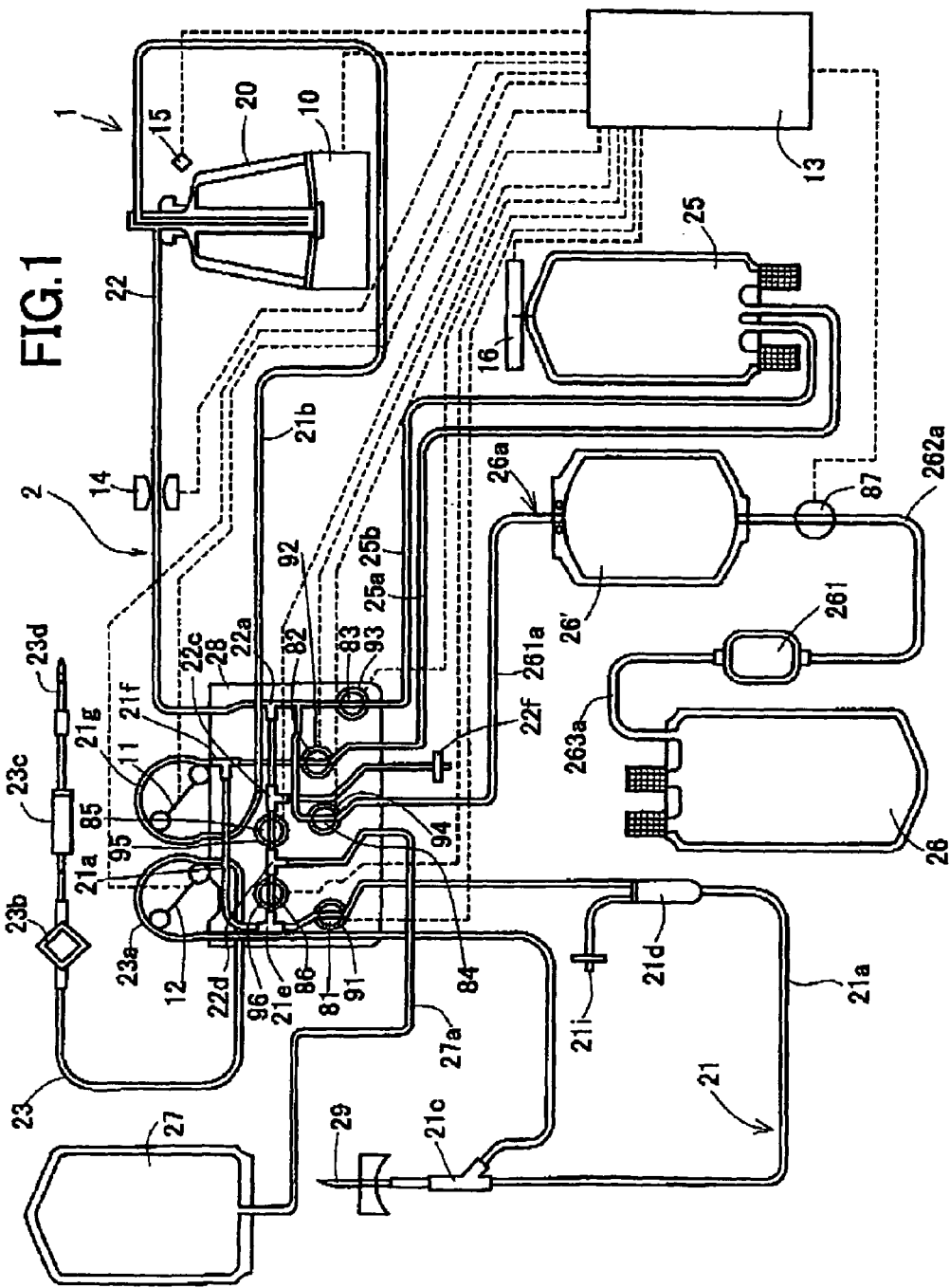
FIG. 1 is a plan view showing the configuration of a blood component collection system according to the present invention.

A blood component collection system according to the present invention will be detailed in conjunction with a preferred embodiment shown in the drawings below.

Figure 2:
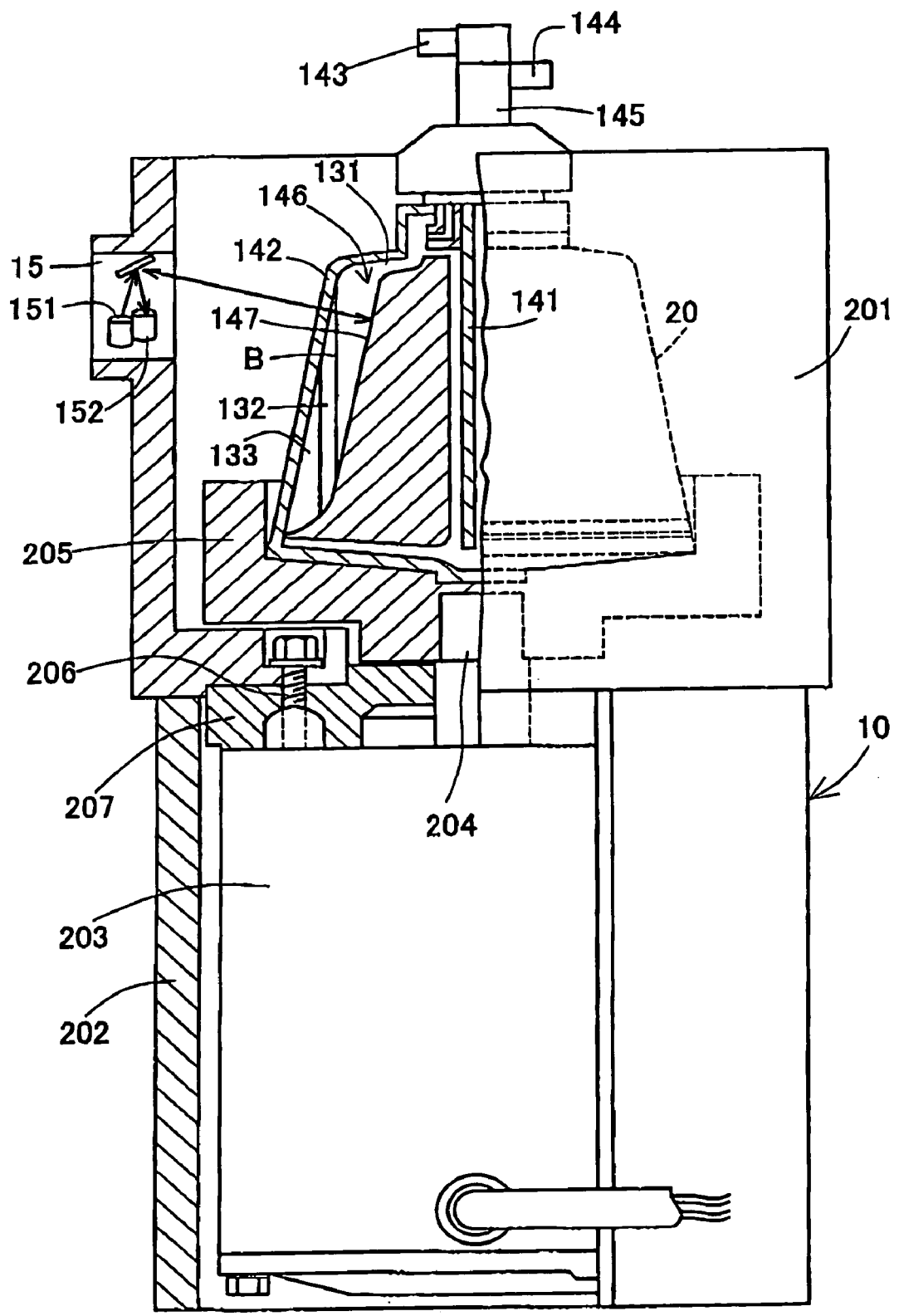
FIG. 2 is a partly cutaway sectional view showing a state in which a centrifugal separator drive is mounted on a centrifugal separator included in the blood component collection system.
Figure 3:
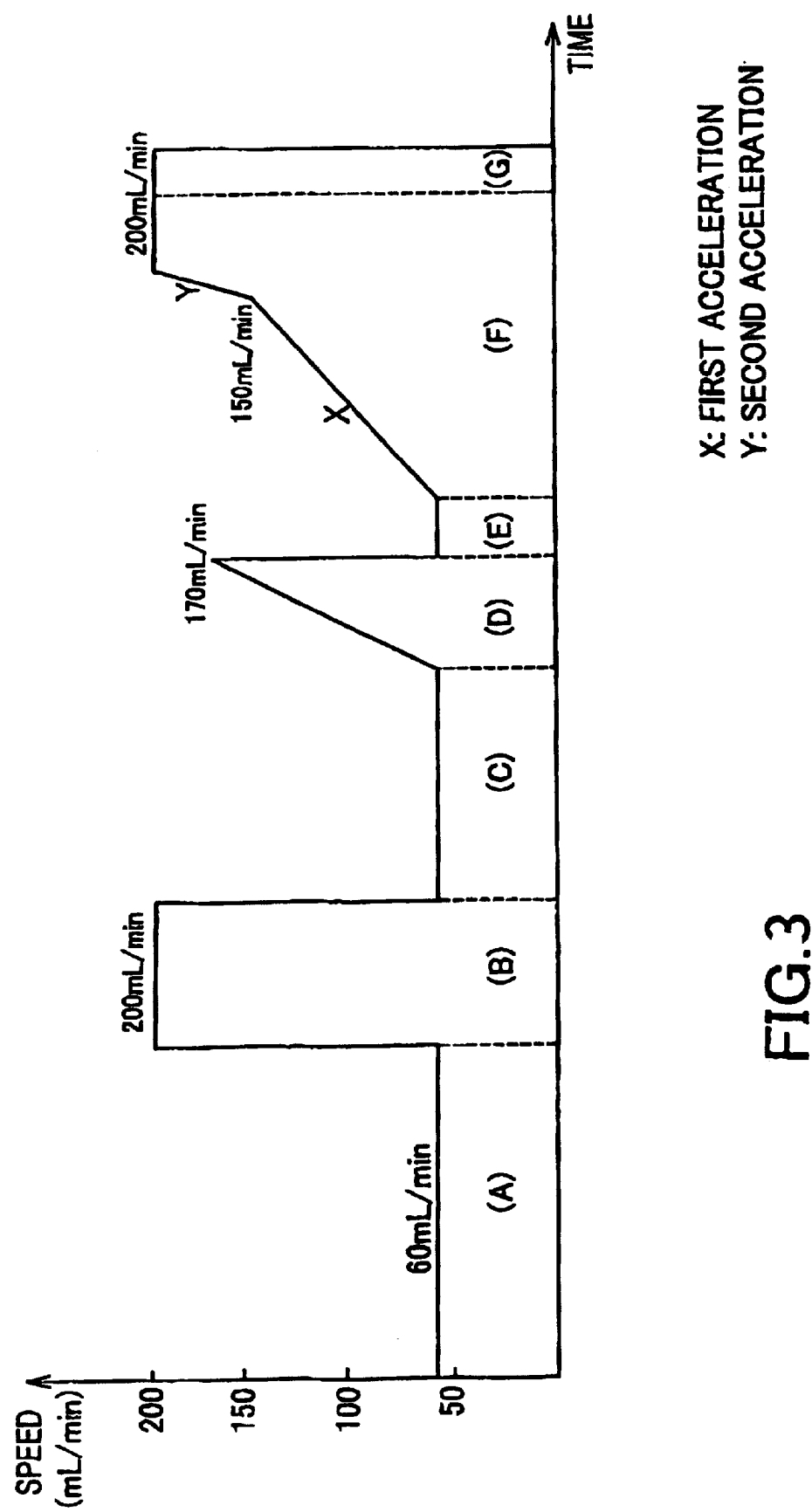
FIG. 3 is a timing chart for explaining the operation of the blood component collection system according to the present invention.

FIG. 1 is a plan view showing the configuration of the blood component collection system according to the present invention. FIG. 2 is a partly cutaway sectional view showing a state in which a centrifugal separator drive is mounted on a centrifugal separator included in the blood component collection system. FIG. 3 is a timing chart for explaining the operation of the blood component collection system according to the present invention. Furthermore, FIG. 4 to FIG. 7 are flowcharts describing the operation of the blood component collection system according to the present invention. FIG. 8 is a flowchart describing the actions the blood component collection system according to the present invention performs for cleansing a line.

The blood component collection system 1 shown in FIG. 1 is a system for separating blood into a plurality of components and collecting any of the separated components (especially platelets). The blood component collection system 1 comprises a centrifugal separator 20 and a blood component collection circuit 2. The centrifugal separator 20 includes a rotor 142 having a blood reservoir space 146 therein and an inlet 143 and an outlet 144 which communicate with the blood reservoir space 146, and centrifuges the blood, which is introduced through the inlet 143 by rotation of the rotor 142, within the blood reservoir space 146. The blood component collection circuit 2 comprises: a first line 21 that links a blood collection needle 29 and the inlet 143 of the centrifugal separator 20; a second line 22 joined to the outlet 144 of the centrifugal separator 20; a third line 23 joined to the first line 21; a plasma collection bag 25 having a first tube 25a joined to the first line 21 and having a second tube 25b joined to the second line 22; a platelet collection bag 26 having a third tube 26a joined to the second line 22; and a buffy coat collection bag 27 having a fourth tube 27a joined to the second line 22.

Furthermore, the blood component collection system 1 comprises: a centrifugal separator drive 10 which rotates the rotor 142 included in the centrifugal separator 20; a first fluid feeder pump 11 for the first line 21; a second fluid feeder pump 12 for the third line 23; a plurality of pieces of channel open/close means 81, 82, 83, 84, 85, 86, and 87 that is used to open or close the middle points of channels defined by the blood component collection circuit 2; a control unit (control means) 13 which controls the centrifugal separator drive 10, first fluid feeder pump 11, second fluid feeder pump 12, and plurality of pieces of channel open/close means 81 to 87; a turbidity sensor 14; an optical sensor 15; and a weight sensor 16.

To begin with, the blood component collection circuit 2 will be described below.

The blood component collection circuit 2 comprises: the first line (blood collection/return line) 21 that links the blood collection needle (blood collecting means) 29 used to collect blood and the inlet 143 of the centrifugal separator 20, and that includes a first pump tube 21g; the second line 22 that links the outlet 144 of the centrifugal separator 20 and the first line 21; the third line (anticoagulant injection line) 23 that is located near the blood collection needle 29 included in the first line 21 and that includes a second pump tube 23a; the plasma collection bag 25 that has the first tube 25a connected on the side of the blood component collection circuit 2 near the blood collection needle 29 beyond the pump tube 21g included in the first line 21, and has the second tube 25b joined to the second line 22; the platelet collection bag 26 that has the third tube 26a joined to the second line 22; and the buffy coat collection bag 27 that has a fourth tube 27a joined to the second line 22.

Incidentally, the blood collecting means is not limited to the blood collection needle 29. Alternatively, a connector (for example, a metallic or synthetic resin needle) coupled to a blood bag or any other blood pool will do.

As the blood collection needle 29, for example, a known metallic needle is adopted.

The first line 21 includes a first blood collection needle-side line 21a joined to the blood collection needle 29 and a first centrifugal separator-side line 21b joined to the inlet 143 of the centrifugal separator 20.

The first blood collection needle-side line 21a has a plurality of soft resin tubes concatenated. The first blood collection needle-side line 21a includes: orderly from the side thereof near the centrifugal separator 20, a branch connector 21c that joins the first blood collection needle-side line 21a and the third line 23; a chamber 21d used to remove bubbles or micro-aggregates; a branch connector 21e that joins the first blood collection needle-side line 21a and the second line 22; and a branch connector 21f that joins the first blood collection needle-side line 21a and the first tube 25a extending from the plasma collection bag 25.

Moreover, an air-permeable and bacteria-impermeable filter 21i is connected to the chamber 21d.

On the other hand, the first centrifugal separator-side line 21b is coupled to the branch connector 21f that joins the first blood collection needle-side line 21a and the first tube 25a, and includes the first pump tube 21g located near the connector.

The second line 22 that links the outlet 144 of the centrifugal separator 20 and the first line 21 has one end thereof coupled to the outlet 144 of the centrifugal separator 20 and the other end thereof coupled to the branch connector 21e of the first line 21.

The second line 22 includes: a branch connector 22a that joins the second line 22, the second tube 25b extending from the plasma collection bag 26, and the third tube 26a extending from the platelet collection bag 26; a branch connector 22c that joins the second line 22 and a tube including a bubble removing filter 22f; and a branch connector 22d that joins the second line 22 and the fourth tube 27a extending from the buffy coat collection bag 27.

The third line 23 has one end thereof coupled to the branch connector 21c included in the first line 21.

The third line 23 includes, orderly from the side thereof coupled to the branch connector 21c, the second pump tube 23a, a bacteria removal filter 23b, a bubble removing chamber 23c, and an anticoagulant container joint needle 23d.

The plasma collection bag (third container) 25 is a container into which plasma (second blood component) is collected (reserved). The plasma collection bag 25 has the first tube 25a coupled to the branch connector 21f which is located on the side of the blood component collection circuit near the blood collection needle 29 beyond the pump tube 21g included in the first line 21. The plasma collection bag 25 also has the second tube 25b coupled to the branch connector 22a included in the second line 22. Namely, the plasma collection bag 25 and second tube 25b constitute a plasma collection branch line used to collect plasma.

The platelet collection bag (second container) 26 is a container into which plasma containing platelets (first blood component) and having passed through a leukoreduction filter 261 that will be described later. The platelet collection bag 26 has the third tube 26a coupled to the branch connector 22a included in the second line 22. Hereinafter, plasma containing platelets (first blood component) shall be called "platelet concentrate (PC)", and the platelet concentrate (PC) collected (reserved) into the platelet collection bag 26 shall be called "a platelet product".

Moreover, a temporary reservoir bag (first container) 26' in which the platelet concentrate (first blood component) is temporarily reserved, and the leukoreduction filter (cell separating filter) 261 that separates or reduce leukocyte (predetermined kind of cells) from the platelet concentrate are inserted into the third tube 26a.

In short, the third tube 26a is composed of three tubes 261a, 262a, and 263a. The tube 261a links the branch connector 22a and the temporary reservoir bag 26'. The tube 262a links the temporary reservoir bag 26' and leukoreduction filter 261. The tube 263a links the leukoreduction filter 261 and the platelet (platelet product) collection bag 26.

The tube 262a serves as a feed tube that feeds platelet concentrate from the temporary reservoir bag 26' to the leukoreduction filter. The tube 263a serves as a release tube that releases the platelet concentrate, which has leukocyte reduced therefrom, from the leukoreduction filter 261 (feeds the platelet concentrate to the platelet collection bag 26).

In other words, the third tube 26 (composed of the tubes 261a, 262a, and 263a), temporary reservoir bag 26', leukoreduction filter 261, and platelet collection bag 26 constitute a platelet collection branch line that collects platelets (platelet product).

Moreover, the temporary reservoir bag 26', leukoreduction filter 261, and platelet collection bag 26 are positioned with the blood component collection system 1 constructed so that the leukoreduction filter 261 will be located at a lower position than the temporary reservoir bag 26' is and the platelet collection bag 26 will be located at a lower position than the leukoreduction filter 261 is.

Moreover, what is used as the leukoreduction filter 261 is, for example, a filter formed by inserting a filtration member into a casing having an inlet and an outlet formed at both ends thereof. The filtration member has one or two layers of a porous substance such as woven cloth, non-woven cloth, mesh, or foam made of a synthetic resin such as polypropylene, polyester, polyurethane, or polyamide.

The buffy coat collection bag 27 is a container into which a buffy coat is collected. The buffer coat bag 27 has the fourth tube 27a coupled to the blanch connector 22d included in the second line 22. Namely, the buffy coat collection bag 27 and fourth tube 27a constitute a buffy coat collection branch line that collects buffy coat.

Preferably, the tubes used to form the first to third lines 21 to 23, pump tubes 21g and 23a, and the tubes 25a, 25b, 26a (composed of the tubes 261a, 262a, and 263a), and 27a coupled to the bags 25 to 27 are made of polyvinyl chloride.

When the tubes are made of polyvinyl chloride, satisfactory flexibility and softness are ensured. The tubes are therefore easy to handle. Moreover, the tubes can be readily blocked using a clamp or the like.

Moreover, the same material as the material made into the tubes can be adopted as the material to be made into the branch connectors 21c, 21e, 21f, 22a, 22c, and 22d.

What are used as the pump tubes 21g and 23a are tubes that are strong enough to remain undamaged even when pressurized by the fluid feeder pumps 11 and 12 (for example, roller pumps) to be described later.

What are used as the plasma collection bag 25, platelet collection bag 26, temporary reservoir bag 26', and buffy coat collection bag 27 are made by layering a flexible resin sheet material and fusing the margins of the layers (through heat fusion, high-frequency fusion, or ultrasonic fusion) in the form of a sac or bonding them using an adhesive in the form thereof.

The material to be made into the bags 25 to 27 and 26' is, for example, soft polyvinyl chloride.

Preferably, the sheet material used to make the platelet collection bag 26 is a material superb in gas permeability in terms of improvement of the ability to reserve platelets in good condition.

Preferably, the sheet material is made of, for example, polyolefin or DnDP flexible polyvinyl chloride. Otherwise, the above resin flexible sheet material may be adopted and made relatively thin (for example, the thickness ranges from about 0.1 mm to about 0.5 mm, or more particularly, from about 0.1 mm to about 0.3 mm).

Moreover, a platelet preservative, for example, GAC, PAS, or PSM-1 may be poured into the plasma collection bag 26 in advance.

The major elements of the blood component collection circuit 2 are, as shown in FIG. 1, provided as cassettes. Namely, the blood component collection circuit 2 has the lines (first line 21, second line 22, and third line 23) and the tubes (first tube 25a, second tube 25b, third tube 26a, and fourth tube 27a) partly stored and preserved, or in other words, partly locked in a cassette housing 28.

Both the ends of the first pump tube 21g and both the ends of the second pump tube 23a are locked in the cassette housing 28. The pump tubes 21g and 23a are projected from the cassette housing 28 in the form of a loop in line with the shape of the fluid feeder pumps (for example, roller pumps) 11 and 12. Consequently, the first and second pump tubes 21g and 23a can be easily attached to the fluid feeder pumps 11 and 12 respectively.

Furthermore, the cassette housing 28 has a plurality of openings 91 to 96 formed therein The centrifugal separator 20 included in the blood component collection circuit 2 is generally called a centrifugal bowl, and designed to separate blood into a plurality of components by utilizing centrifugal force.

The centrifugal separator 20 comprises, as shown in FIG. 2, a pipe 141 extending vertically and having the inlet 143 formed at the upper end thereof, and a hollow rotor 142 that rotates about the pipe 141 and is sealed off from an upper part 145 in a fluid-tight manner.

The rotor 142 has the annular blood reservoir space 146 formed along the internal surface of the circumferential wall thereof. The blood reservoir space 146, is shaped (tapered) so that the inner and outer diameters thereof will gradually diminish from the lower part thereof shown in FIG. 2 to the upper part thereof. The lower part of the blood reservoir space 146 communicates with the lower-end opening of the pipe 141 by way of a substantially disk-like channel formed on the bottom of the rotor 142. The upper part of the blood reservoir space 146 communicates with the outlet 144. Moreover, the volume of the blood reservoir space 146 included in the rotor 142 ranges, for example, from about 100 mL to about 350 mL. The maximum inner diameter (maximum radius) of the blood reservoir space with the axis of rotation of the rotor 142 as a center ranges, for example, from about 55 mm to about 65 mm.

The rotor 142 is rotated under predetermined conditions for centrifugation (rotating speed and rotation time) predetermined by the centrifugal separator drive 10 included in the blood component collection system 1. Under the conditions for centrifugation, a blood separation pattern (for example, the number of blood components to be separated) can be determined for blood introduced into the rotor 142.

According to the present embodiment, the conditions for centrifugation are determined so that blood will be, as shown in FIG. 2, separated into, orderly from the innermost layer, a layer of plasma 131, a buffy coat layer 132, and a layer of red blood cells 133.

Next, the overall configuration of the blood component collection system 1 shown in FIG. 1 will be described below.

The blood component collection system 1 comprises: the centrifugal separator drive 10 that rotates the rotor 142 included in the centrifugal separator 20; the first fluid feeder pump 11 located in the middle of the first line 21; the second fluid feeder pump 12 located in the middle of the third line 23; the plurality of pieces of channel open/close means 81, 82, 83, 84, 85, 86, and 87 that can open or close the middles of the channels defined by (the first line 21, second line 22, first tube 25*a*, second tube 25*b*, and third tube 26*a* included in) the blood component collection circuit 2;

and the control unit (control means) 13 that controls the centrifugal separator drive 10, first fluid feeder pump 11, second fluid feeder pump 12, and plurality of pieces of channel open/close means 81 to 87.

Furthermore, the blood component collection system 1 comprises: the turbidity sensor 14 attached to (included in) the second line 22 on the side of the second line near the centrifugal separator 20 (upstream) beyond the connector 22*a* that joins the second line 22 and the second tube 25*b*; the optical sensor 15 located near the centrifugal separator 20; and the weight sensor 16 that measures the weight of plasma together with the weight of the plasma collection bag 25.

The control unit 13 includes two pump controllers (not shown) that control the first fluid feeder pump 11 and second fluid feeder pump 12 respectively. The control unit 13 is electrically connected to the first fluid feeder pump 11 and second fluid feeder pump 12 via the respective pump controllers.

A driving controller (not shown) included in the centrifugal separator drive 10 is electrically connected to the control unit 13.

The pieces of channel open/close means 81 to 87 are electrically connected to the control unit 13.

The turbidity sensor 14, optical sensor 15, and weight sensor 16 are electrically connected to the control unit 13.

The control unit 13 is formed with, for example, a microcomputer, and receives detection signals from the turbidity sensor 14, optical sensor 15, and weight sensor 16 respectively at any time.

Based on the detection signals received from the turbidity sensor 14, optical senior 15, and weight sensor 16 respectively, the control unit 13 activates the components of the blood component collection system 1 according to a pre-installed program. Specifically, the control unit 13 controls the start or stop of the rotations of the fluid feeder pumps 11 and 12, and the direction of rotation (forward rotation or reverse rotation). Moreover, if necessary, the control unit 13 controls the open or close of the pieces of channel open/close means 81 to 87 and the activation of the centrifugal separator drive 10.

The first channel open/close means 81 opens or closes the first line 21 while being located on the side of the blood component collection circuit near the blood collection needle 29 beyond the first pump tube 21*g*.

The second channel open/close means 82 opens or closes the first tube 25*a* extending from the plasma collection bag 25.

The third channel open/close means 83 opens or closes the second tube 25*b* extending from the plasma collection bag 25.

The fourth channel open/close means 84 opens or closes the third tube 26*a* (tube 261*a*) extending from the platelet collection bag 26.

The fifth channel open/close means 85 opens or closes the second line 22 while being located on the side (upstream) of the blood component collection circuit near the centrifugal separator 20 beyond the connector (branch connector 22*d*) that joins the second line 22 and the fourth tube 27*a* extending from the buffy coat collection bag 27.

The sixth channel open/close means 86 opens or closes the second line 22 while being interposed between the connector (branch connector 21*e*) that joins the first line 21 and second line 22, and the connector (branch connector 22*d*) that joins the second line 22 and the fourth tube 27*a* (downstream the connector that joins the second line 22 and fourth tube 27*a*).

Moreover, the seventh channel open/close means 87 opens or closes the third tube 26*a* (tube 262*a*).

The pieces of channel open/close means 81 to 87 each have an insertion member into which the first line 21, second line 22, first tube 25*a*, second tube 25*b*, or third tube 26*a* (tube 261*a* or 262*a*) can be inserted. The insertion member includes a clamp that is actuated by a driving source, for example, a solenoid, an electric motor, or a (hydraulic or pneumatic) cylinder. More particularly, an electromagnetic clamp to be actuated by a solenoid is preferred.

The pieces of channel open/close means (clamps) 81 to 87 are actuated based on a signal sent from the control unit 13.

The centrifugal separator drive 10 comprises, as shown in FIG. 2, a housing 201 in which the centrifugal separator 20 is stored, legs 202, a motor 203 that is a driving source, and a disk-like locking base 205 that bears the centrifugal separator 20.

The housing 201 is placed on and fixed to the tops of the legs 202. Moreover, the motor 203 is fixed to the bottom of the housing 201 using a bolt 206 with a spacer 207 between them.

The locking base 205 is engaged with the distal part of a rotation shaft 204 of the motor 203 so that the locking base 205 will be rotated concentrically and together with the rotation shaft 204. A concave part in which the bottom of the rotor 142 is fitted is formed in the upper surface of the locking base 25.

Moreover, the upper part 145 of the centrifugal separator 20 is fixed to the housing 201 using a fixing member that is not shown.

In the centrifugal separator drive 10 having the foregoing components, when the motor 23 is driven, the locking base 205 and the rotor 142 fixed to the locking base 205 are rotated at, for example, a rotational frequency ranging from about 3000 rpm to about 6000 rpm.

The optical sensor 15 is located on the side (left side in FIG. 2) of the housing 201.

The optical sensor 15 is designed to irradiate light to the blood reservoir space 146 and receive light reflected therefrom.

In the optical sensor 15, light (for example, laser light) is irradiated from a floodlight 151. A light receiver 152 receives light reflected from the reflecting surface 147 of the rotor 142. The light receiver 152 converts the received light into an electric signal whose level is proportional to the amount of received light.

At this time, the irradiated light and reflected light pass through the blood components in the blood reservoir space 146. However, the abundance ratio of each blood component varies depending on the position of the interface between the blood component and an adjoining blood component (in the present embodiment, the interface B between the layer of plasma 131 and the buffy coat layer 132) through which the irradiated light or reflected light passes. For this reason, the transmittance of each blood component varies depending on the position. Accordingly, the amount of light received by the light receiver 152 varies (changes). The variation is detected as a change in output voltage sent from the light receiver 152.

In short, the optical sensor 15 can detect the position of the interface between adjoining blood components according to a change in the amount of light received by the light receiver 152.

The interface between adjoining blood components whose position is detected by the optical sensor 15 is not limited to the interface B but may be the interface between, for example, the buffy coat layer 132 and the layer of red blood cells 133.

Now, the layers 131 to 133 in the blood reservoir space 146 are different from one another in terms of color because of the difference among the blood components. In particular, the layer of red blood cells 133 is reddish because red blood cells are red. Consequently, from the viewpoint of improvement in precision to be offered by the optical sensor 15, light serving as irradiated light should preferably have a spectrum ranging, for example, from about 600 nm to about 900 nm, or more preferably, from about 750 nm to about 800 nm, though it is not limited to the range.

The turbidity sensor 14 senses the turbidity of a fluid flowing through the second line 22 and transmits a voltage inversely proportional to a degree of turbidity. Specifically, when the degree of turbidity is high, the turbidity sensor 14 transmits a low voltage. When the degree of turbidity is low, the turbidity sensor 14 transmits a high voltage.

Owing to the turbidity sensor 14, for example, a change of a fluid flowing through the second line 22 from air to plasma, a change in the concentration of platelets in plasma, or mixture of red blood cells in plasma can be detected.

As the first fluid feeder pump 11 to which the first pump tube 21g is attached and the second fluid feeder pump 12 to which the second pump tube 23a is attached, a non-blood contact pump, for example, a roller pump is adopted preferably.

Moreover, as the first fluid feeder pump (blood pump) 11, a pump capable of feeding blood in either directions is adopted. Specifically, a roller pump capable of rotating forward and reversely is adopted.

Next, referring to FIG. 1, FIG. 3, and FIG. 4 to FIG. 8 that are flowcharts, blood component collection to be performed using the blood component collection system 1 will be described by taking for instance a case where platelets are collected. FIG. 3 is a timing chart outlining a first cycle of blood component collection to be performed using the blood component collection system 1.

The blood component collection system 1 acts to execute platelet collection composed of, as shown in FIG. 3, a first plasma collection process (A), a constant-speed plasma circulation process (B), a second plasma collection process (C), an accelerated plasma circulation process (D), a third plasma collection process (E), a platelet collection step (F), and a blood return step.

Moreover, according to the present embodiment, the platelet collection is repeated three times (first cycle to third cycle). Furthermore, a buffy coat collection process (G) is executed prior to the blood return process after the completion of the platelet collection process (F) within each cycle other than the final (third) cycle. A buffy coat return process is executed prior to the first plasma collection process (A) within the next platelet collection.

According to the present invention, in the blood component collection system 1, concurrently with the final cycle of platelet collection, platelet concentrate temporarily collected (reserved) in the temporary reservoir bag 26' is fed to the leukoreduction filter 261, and filtered to have leukocyte separated or reduced therefrom (see S401 in FIG. 8). From the viewpoint of shortening the binding time during which a donor is bound, the filtration should preferably be started concurrently with the final cycle of platelet collection (in particular, in an early process within platelet collection). In the blood component collection system 1 of the present embodiment, the filtration is started nearly concurrently with the second plasma collection process (C) within the final cycle of platelet collection.

First, the third line 23 and blood collection needle 29 are primed with an anticoagulant. Thereafter, a donor's, vessel is punctured with the blood collection needle 29.

Figure 4:
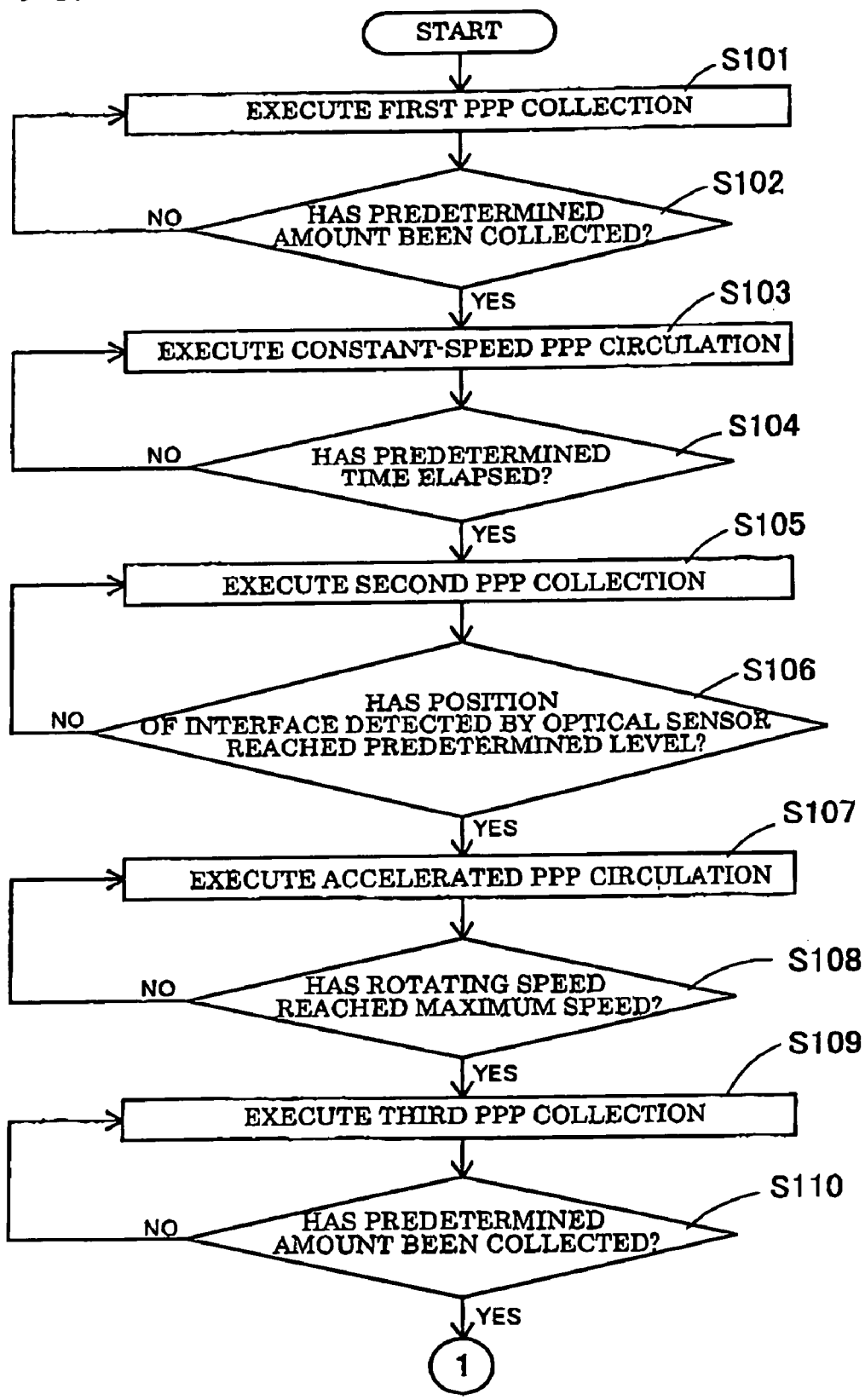
FIG. 4 is a flowchart describing the operation of the blood component collection system according to the present invention.
Figure 5:
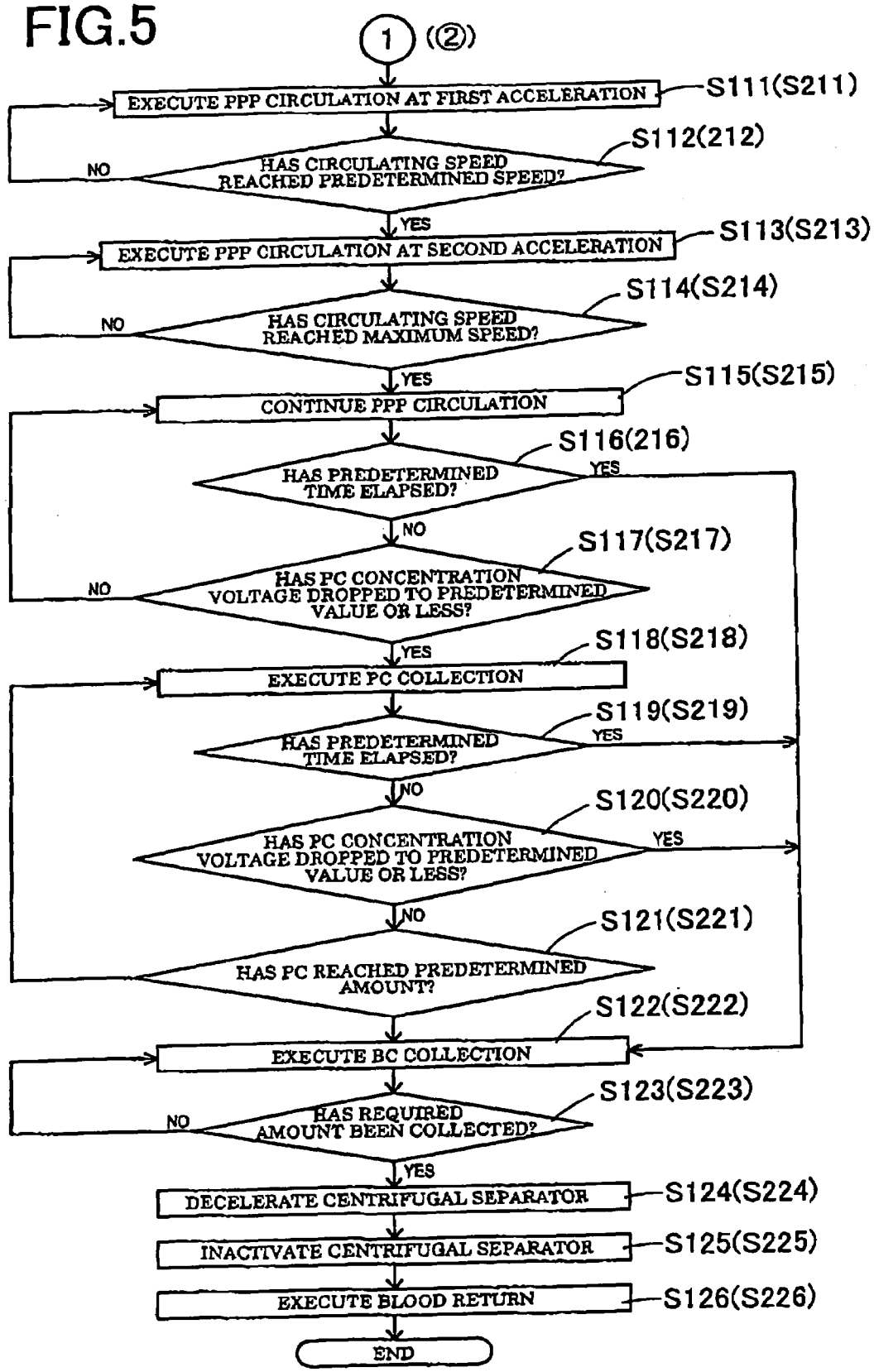
FIG. 5 is a flowchart describing the operation of the blood component collection system according to the present invention.

[1] First cycle of platelet collection (see FIG. 4 and FIG. 5)

[11] First, the blood component collection system 1 executes the first plasma collection (first PPP collection) process (A). In the first plasma collection process (A), blood is routed to the blood reservoir space 146 of the rotor 142, and centrifuged. Consequently, separated plasma (PPP) is collected into the plasma collection bag 25.

In the first plasma collection process (A), first, the control unit 13 executes plasma (second blood component) collection (step S101 in FIG. 4).

Specifically, the first channel open/close means 81 and fourth channel open/close means 84 are unblocked under the control of the control unit 13, but the other pieces of channel open/close means are left blocked. In this state, the first fluid feeder pump 11 is actuated (rotated forward) at a predetermined rotating speed (preferably, about 250 mL/min or less, or more preferably, from about 40 mL/min to about 150 mL/min, and in the present embodiment, 60 mL/min). Thus, blood is collected from the donor.

Concurrently with the blood collection, the second fluid feeder pump 12 is actuated under the control of the control unit 13. An anticoagulant, for example, an ACD-A solution is fed through the third line 23, and mixed in the collected blood.

At this time, the control unit 13 controls the rotating speed of the second fluid feeder pump 12 so that the anticoagulant will be mixed in the collected blood at a predetermined ratio (preferably, about 1/20 to about 1/6, for example, 1/10).

Consequently, the blood (anticoagulant-inclusive blood) is carried through the first line 21. The blood then enters the inlet 143 of the centrifugal separator 20, passes through the pipe 141, and is thus routed to the blood reservoir space 146 of the rotor 142.

At this time, the air (sterilized air) in the centrifugal separator 20 is fed to the temporary reservoir bag 26' by way of the second line 22 and third tube 26a.

Concurrently with the blood collection, or before or after the blood collection, the control unit 13 actuates the centrifugal separator drive 10 and rotates the rotor 142 at a predetermined rotational frequency.

With the rotation of the rotor 142, the blood introduced into the blood reservoir space 146 is separated into the layer of plasma (PPP) 131, buffy coat layer (BC) 132, and layer of red blood cells (CRC) 133 in that order from the innermost layer.

The rotational frequency of the rotor 142 ranges, preferably, from about 3000 rpm to about 6000 rpm, or more preferably, from about 4200 rpm to about 5800 rpm. Moreover, in the processes described below, the control unit 13 does not change the rotational frequency of the rotor 142 unless otherwise described.

Furthermore, the blood collection and the feed of an anticoagulant are continued. When an amount of blood (approx. 270 mL) exceeding the capacity of the blood reservoir space 146 is routed to the blood reservoir space 146, the blood reservoir space 146 is filled with blood, and plasma (PPP) overflows through the outlet 144 of the centrifugal separator 20.

At this time, the turbidity sensor 14 attached to the second line 22 detects that a fluid flowing through the second line 22 has changed. from air to plasma. Based on the detection signal sent from the turbidity sensor 14, the control unit 13 blocks the fourth channel open/close means 84 and unblocks the third channel open/close means 83.

Consequently, plasma is routed or collected into the plasma collection bag (third container) 25 by way of the second line 22 and second tube 25b.

The weight sensor 16 measures the weight of the plasma collection bag 25. A weight signal representing the measured weight is transferred to the control unit 13.

Thereafter, the control unit 13 judges from the information (weight signal) sent from the weight sensor 16 whether a predetermined amount of plasma has been collected into the plasma collection bag 25 (step S102 in FIG. 4).

The (predetermined) collected amount of plasma ranges, preferably, from about 10 g to about 150 g, or more preferably, from about 20 g to about 40 g.

If it is found at step S102 that the predetermined amount of plasma has not been collected into the plasma collection bag 25, the control unit 13 returns to step S101, and repeats step S101 and subsequent steps.

If it is found at step S102 that the predetermined amount of plasma has been collected into the plasma collection bag 25, the control unit 13 terminates the process [11] (first plasma collection process (A)), and proceeds to the constant-speed plasma circulation process (B).

[12] Thereafter, the blood component collection system 1 executes the constant-speed plasma circulation (constant-speed PPP circulation) process (B). In the constant-speed plasma circulation process (B), the plasma in the plasma collection bag 25 is circulated through the blood reservoir space 146 at a constant speed.

In the constant-speed plasma circulation process (B), first, the control unit 13 executes plasma circulation (step S103 in FIG. 4).

Specifically, under the control of the control unit 13, the first channel open/close means 81 is blocked and the second channel open/close means 82 is unblocked. Moreover, the second fluid feeder pump 12 is inactivated, and the first fluid feeder pump 11 is actuated (rotated forward) at a predetermined rotating speed (preferably, from about 60 mL/min to about 250 mL/min, and in the present embodiment, 200 mL/min).

Consequently, blood collection is suspended. The plasma in the plasma collection bag 25 is routed to the blood reservoir space 146 by way of the first tube 25a and first line 21 at a constant speed. Plasma flowing out of the outlet 144 of the centrifugal separator 20 is collected into the plasma collection bag 25 by way of the second line 22 and second tube 25b.

In short, the plasma in the plasma collection bag 25 is circulated through the blood reservoir space 146 at the constant speed.

Thereafter, the control unit 13 judges whether a predetermined time (preferably, from about 10 sec to about 90 sec, for example, 30 sec) has elapsed since the start of the constant-speed plasma circulation (step S104 in FIG. 4).

If it is found at step S104 that the predetermined time has not elapsed since the start of the constant-speed plasma circulation, the control unit 13 returns to step S103, and repeats step S103 and subsequent steps.

If it is found at step S104 that the predetermined time has elapsed since the start of the constant speed plasma circulation, the control unit 13 terminates the process [12] (constant-speed plasma circulation process (B)), and proceeds to the second plasma collection process (C).

[13] Thereafter, the blood component collection system 1 executes the second plasma (PPP) collection process (C). In the second plasma collection process (C), blood is routed to the blood reservoir space 146 of the rotor 142 and centrifuged. Separated plasma is then collected into the plasma collection bag 25.

In the second plasma collection process (C), the same steps as those included in the process [11] (first plasma collection process (A)) are executed except the step of measuring a collected amount of plasma using the weight sensor 16. Instead of the step, the position of the interface between the layer of plasma 131 and the buffy coat layer 132 is detected.

In the second plasma collection process (C), first, the control unit 13 collects plasma (step S105 in FIG. 4).

At this time, the control unit 13 blocks the second channel open/close means 82 and unblocks the first channel open/close means 81.

Consequently, the number of red blood cells in the blood reservoir space 146 increases, that is, the thickness of the layer of red blood cells 133 increases. Accordingly, the interface B rises gradually (moves towards the axis of rotation of the rotor 142).

Thereafter, the control unit 13 judges from the detection signal sent from the optical sensor 15 (information of the detected interface position) whether the interface B has reached a predetermined level (first position) (step S106 in FIG. 4).

Incidentally, the first position of the interface B is a position at which the detection signal sent from the first optical sensor 15 (an output voltage sent from the light receiver 152) ranges, preferably, from about 1 V to about 2 V.

If it is found at step S106 that the interface B has not reached the first position, the control unit 13 returns to step S105, and repeats step S105 and subsequent steps.

Moreover, if it is found at step S105 that the interface B has reached the first position, the control unit 13 terminates the present process [13] (second plasma collection process (C)) and proceeds to the accelerated plasma circulation process (D).

[14] Thereafter, the blood component collection system 1 executes the accelerated plasma (PPP) circulation process (D). In the accelerated plasma (PPP) circulation process (D), the plasma in the plasma collection bag 25 is circulated through the blood reservoir space 146 while being accelerated.

In the accelerated plasma (PPP) circulation process (D), first, the control unit 13 executes plasma circulation (step S107 in FIG. 4).

Specifically, the first channel open/close means 81 is blocked under the control of the control unit 13, and the second channel open/close means 82 is unblocked thereunder. Moreover, the second fluid feeder pump 12 is inactivated, and the first fluid feeder pump 11 is activated (rotated forward) so that the rotating speed thereof will increase at a rate corresponding to a constant acceleration.

Consequently, blood collection is suspended. Moreover, the plasma in the plasma collection bag 25 is routed to the blood reservoir space 146 by way of the first tube 25a and first line 21 while being accelerated. Plasma flowing out of the outlet 144 of the centrifugal separator 20 is collected into the plasma collection bag 25 by way of the second line 22 and second tube 25b. In short, the plasma in the plasma collection bag 25 is circulated through the blood reservoir space 146 while being accelerated.

At this time, the control unit 13 extends control so that the rotating speed of the first fluid feeder pump 11 will increase at a rate corresponding to a constant acceleration from a speed lower than the speed attained during the constant-speed plasma circulation (initial speed is, in the present embodiment, 60 mL/min).

The condition for acceleration (acceleration) ranges, preferably, from about 1 mL/min/sec to 10 mL/min/sec, or more preferably, from about 3 mL/min/sec to about 6 mL/min/sec. In the present embodiment, the acceleration is set to a fixed value. Alternatively, the acceleration may be varied stepwise or continuously within the above range.

Thereafter, the control unit 13 judges whether the circulating speed at which plasma circulates through the blood reservoir space 146 has reached the maximum speed, that is, whether the rotating speed of the first fluid feeder pump 11 has reached the maximum speed (preferably, from about 130 mL/min to 250 mL/min, and in the present embodiment, 170 mL/min) (step S108 in FIG. 4).

The step S108 is continued until the circulating speed at which plasma circulates through the blood reservoir space 146 reaches the maximum speed.

If it is found at step S108 that the circulating speed at which plasma circulates through the blood reservoir space 146 has reached the maximum speed, the control unit 13 terminates the present process [14] (accelerated plasma circulation process (D)) and proceeds to the third plasma collection process (E);

[15] Thereafter, the blood component collection system 1 executes the third plasma (PPP) collection process (E). In the third plasma collection process (E), blood is routed to the blood reservoir space 146 of the rotor 142 and centrifuged. Separated plasma is collected into the plasma collection bag 25.

In the third plasma collection process (E), first, the control unit 13 executes plasma collection (step S109 in FIG. 4).

Thereafter, the control unit 13 judges from the information (weight signal) sent from the weight sensor 16 whether a predetermined amount of plasma has been collected into the plasma collection bag 25 (step S110 in FIG. 4).

The (predetermined) collected amount of plasma ranges, preferably, from about 2 g to about 30 g, or more preferably, from about 5 g to about 15 g.

If it is found at step S110 that the predetermined amount of plasma has been collected into the plasma collection bag 25, the control unit 13 terminates the present process [15] (third plasma collection process (E)) and proceeds to the plasma collection process (F) (① in FIG. 5).

[16] Thereafter, the blood component collection system 1 executes the platelet (PC) collection process (F). In the platelet collection process (F), the plasma in the plasma collection bag 25 is circulated through the blood reservoir space 146 while being accelerated at a first acceleration. Thereafter, the first acceleration is changed to a second acceleration that is higher than the first acceleration. The plasma is circulated while being accelerated at the second acceleration. This causes platelets to flow out of the blood reservoir space 146. Consequently, platelet concentrate is collected (reserved) into the temporary reservoir bag 26'.

In the platelet collection process, first, the control unit 13 executes plasma (PPP) circulation at the first acceleration (first acceleration step in FIG. 3, step S111 in FIG. 5).

Specifically, the first channel open/close means 81 is blocked under the control of the control unit 13, and the second channel open/close means 82 is unblocked thereunder. The second fluid feeder pump 12 is inactivated, and the first fluid feeder pump 11 is activated (rotated forward) so that the rotating speed thereof will increase at a rate corresponding to the first acceleration.

Consequently, blood collection is suspended. Moreover, the plasma in the plasma collection bag 25 is routed to the blood reservoir space 146 by way of the first tube 25a and first line 21 while being accelerated at the first acceleration. Plasma flowing out of the outlet 144 of the centrifugal separator 20 is collected into the plasma collection bag 25 by way of the second line 22 and second tube 25b. In short, the plasma in the plasma collection bag 25 is circulated through the blood reservoir space 146 while being accelerated at the first acceleration.

At this time, when plasma is circulated through the blood reservoir space 146 while being accelerated at the first acceleration, the thickness of the layer of red blood cells 133 increases. Consequently, the interface B rises gradually (moves toward the axis of rotation of the rotor 142).

The first acceleration ranges, preferably, from about 0.5 mL/min/sec to about 10 mL/min/sec, or more preferably, from about 1.5 mL/min/sec to about 2.5 mL/min/sec. In the present embodiment, the first acceleration is set to a fixed value. Alternatively, the first acceleration may be varied stepwise or continuously within the above range.

Moreover, the initial rotating speed of the first fluid feeder pump 11 for circulating plasma at the first acceleration ranges, preferably, from about 40 mL/min to about 150 mL/min, or more preferably, from about 50 mL/min to about 80 mL/min. In the present embodiment, the initial rotating speed of the first fluid feeder pump 11 is set to 60 mL/min.

Thereafter, the control unit 13 continues step S111 until the circulating speed at which plasma circulates through the blood reservoir space 146 reaches a predetermined speed (step S112 in FIG. 5).

Incidentally, the circulating speed of plasma, that is, the rotating speed of the first fluid feeder pump 11 ranges, preferably, from about 100 mL/min to about 180 mL/min, or more preferably, from about 140 mL/min to about 160 mL/min. In the present embodiment, the rotating speed of the first fluid feeder pump 11 is set to 150 mL/min.

If it is found at step S112 that the circulating speed at which plasma circulates through the blood reservoir space 146 has reached the predetermined speed, the control unit 13 executes plasma (PPP) circulation at a second acceleration speed (first acceleration step in 3, step S113 in FIG. 5).

Specifically, the acceleration of the first fluid feeder pump 11 is changed from the first acceleration to the second acceleration under the control of the control unit 13. Moreover, the first fluid feeder pump 11 is activated (rotated forward) so that the rotating speed thereof will increase at a rate corresponding to the second acceleration. Consequently, the plasma in the plasma collection bag 25 is circulated through the blood reservoir space 146 while being accelerated at the second acceleration.

When the plasma is circulated through the blood reservoir space 146 while being accelerated at the second acceleration, the thickness of the layer of red blood cells 133 increases, and the interface B rises gradually (moves toward the axis of rotation of the rotor 142). Moreover, the platelets (PC) contained in the buffy coat layer 132 floats (goes up) against centrifugal force, and moves toward the outlet 144 of the rotor 142.

The second acceleration is determined to be higher than the first acceleration, and ranges, preferably, from about 3 mL/min/sec to about 20 mL/min/sec, or more preferably, from about 5 mL/ruin/sec to about 10 mL/min/sec. In the present embodiment, the second acceleration is set to a fixed value. Alternatively, the second acceleration may be varied stepwise or continuously within the range.

Thereafter, the control unit 13 judges whether the circulating speed at which plasma circulates through the blood reservoir space 146 has reached the maximum speed, that is, whether the rotating speed of the first fluid feeder pump 11 has reached the maximum speed (preferably, from about 120 mL/min to 300 mL/min, and in the present embodiment, 200 mL/min) (step S114 in FIG. 5).

If it is found at step S114 that the circulating speed at which plasma circulates through the blood reservoir space 146 has not reached the maximum speed, the control unit 13 returns to step S113, and repeats step S113 and subsequent steps.

If it is found at step S114 that the circulating speed at which plasma circulates through the blood reservoir space 146 has reached the maximum speed, the control unit 13 continues plasma (PPP) circulation (step S115 in FIG. 5).

Specifically, the control unit 13 extends control so that the rotating speed of the first fluid feeder pump 11 will be retained (held) at the maximum speed attained at step S115. Consequently, the circulating speed at which plasma circulates through the blood reservoir space 146 ranges, preferably, from about 120 mL/min to about 300 mL/min. In the present embodiment, the circulating speed is set to 200 mL/min.

Thereafter, the control unit 13 judges whether a predetermined time (preferably, from about 5 sec to about 15 sec, for example, 10 sec) has elapsed since the continuation of plasma circulation is determined (step S116 in FIG. 5).

If it is found at step S116 that the predetermined time has not elapsed since the continuation of plasma circulation is determined, the control unit 13 judges whether the output voltage (PC concentration voltage) sent from the turbidity sensor 14 had dropped to a predetermined value (preferably, from about 2.5 V to about 3.5 V, for example, 3.0 V) or less (step S117 in FIG. 5), If it is found at step S117 that the output voltage sent from the turbidity sensor 14 has not dropped to the predetermined value or less, the control unit 13 returns to step S115 and repeats step S115 and subsequent steps.

While steps S115 to S117 are repeated, if it is found at step S116 that the predetermined time has elapsed since the continuation of plasma circulation is determined, the control unit 13 terminates the present process [16] (platelet collection process (F)) and proceeds to the buffy coat collection process (G).

If it is found at step S117 that the output voltage sent from the turbidity sensor 14 has dropped to the predetermined value or less, that is, if the concentration of platelets contained in plasma which flows through the second line 22 along with the outflow of platelets from the outlet 144 of the rotor 142 has reached a predetermined value or more, the control unit 13 executes platelet (PC) collection (step S118 in FIG. 5).

Specifically, based on the detection signal sent from the turbidity sensor 14, the control unit 13 blocks the third channel open/close means 88 and unblocks the fourth channel open/close means 84.

Consequently, platelet concentrate is routed to the temporary reservoir bag 26' by way of the second line 22 and third tube 26a (tube 261a), and collected (reserved). At this time, since the seventh channel open/close means 87 is blocked, the platelet concentrate does not flow out of the temporary reservoir bag 26'.

Moreover, the control unit 13 calculates the concentration of platelets (concentration of cumulative platelets) in the temporary reservoir bag 26' according to the output voltage (detection signal) sent from the turbidity sensor 14. The concentration of platelets keeps rising after the start of platelet collection. Once the concentration of platelets reaches the maximum value, it decreases.

Thereafter, the control unit 13 judges whether a predetermined time (preferably, from about 10 sec to about 25 sec, for example, 15 sec) has elapsed since the start of PC collection (step S119 in FIG. 5).

If it is found at step S119 that the predetermined time has not elapsed since the start of platelet collection, the control unit 13 judges whether the output voltage sent from the turbidity sensor 14 (platelet (PC) concentration voltage) has reached a predetermined value or less (step S120 in FIG. 5).

The predetermined value of the output voltage sent from the turbidity sensor 14 is a value near the value of the output voltage transmitted when red blood cells (CRC) are mixed in plasma flowing through the second line 22, or preferably, about 0.5 V or less.

If it is found at step S120 that the output voltage sent from the turbidity sensor 14 has not reached the predetermined value or less, the control unit 13 judges whether the amount of platelet concentrate in the temporary reservoir bag 26' has reached a predetermined amount (step S121 in FIG. 5).

Incidentally, the collected (predetermined) amount of platelet concentrate ranges, preferably, about 20 mL to about 100 mL, or more preferably, from about 40 mL to about 70 mL.

If it is found at step S121 that the platelet concentrate in the temporary reservoir bag 26' has not reached the predetermined amount, the control unit 13 returns to step S118 and repeats step S118 and subsequent steps.

While steps S118 to S121 are repeated, if it is found at step S119 that the predetermined time has elapsed since the start of platelet collection, or if it is found at step S120 that the output voltage sent from the turbidity sensor 14 has reached the predetermined value or less, the control unit 13 terminates the present process [16] (platelet collection process (F)) and proceeds to the buffy coat collection process (G).

If it is found at step S121 that the platelet concentrate in the temporary reservoir bag 26' has reached the predetermined amount, the control unit 13 terminates the present process [16] (platelet collection process (F)) and proceeds to the buffy coat collection process (G).

[17] Thereafter, the blood component collection system 1 executes the buffy coat (BC) collection process (G). In the buffy coat (BC) collection process (G), a buffy coat is caused to flow out of the blood reservoir space 146 of the rotor 142 and collected.

In the buffy coat collection process (G), first, the control unit 13 executes buffy coat collection (step S122 in FIG. 5).

Specifically, the fourth channel open/close means 84 is blocked under the control of the control unit 13, and the fifth channel open/close means 85 is unblocked thereunder. The first fluid feeder pump 11 is activated (rotated forward) at the predetermined rotating speed (preferably, from about 60 mL/min to about 300 mL/min, and in the present embodiment, 200 mL/min).

Consequently, the plasma in the plasma collection bag 25 is routed to the blood reservoir space 146 at the predetermined speed by way of the first tube 25a and first line 21. The buffy coat flowing out of the outlet 144 of the rotor 142 is routed and collected into the buffy coat collection bag 27 by way of the second line 22 and fourth tube 27a.

In the buffy coat collection process (G), the control unit 13 changes the rotational frequency of the rotor 142.

The rotational frequency of the rotor 142 is set to be lower than the rotational frequency thereof set in the aforesaid processes [11] to [16] by, for example, a value ranging from about 100 rpm to about 300 rpm. Specifically, the rotational frequency ranging from about 4500 rpm to about 4600 rpm is preferred.

Thereafter, the control unit 13 judges whether a predetermined amount of a buffy coat has been collected into the buffy coat collection bag 27 (step S123 in FIG. 5).

Specifically, the control unit 13 calculates a collected (predetermined) amount of a buffy coat according to an amount of collected blood, a donor's hematocrit, and the number of platelets collected in the platelet collection process. The control unit 13 then determines the number of rotations, by which the first fluid feeder pump 11 should be rotated, on the basis of the calculated acquired amount. The control unit 13 then judges whether the first fluid feeder pump 11 has rotated by the number of rotations required to collect the calculated collected amount.

If it is found at step S123 that the predetermined amount of a buffy coat has not been collected into the buffy coat collection bag 27, that is, if the first fluid feeder pump 11 has not been rotated by the required number of rotations, the control unit 13 returns to step S122 and repeats step S122 and subsequent steps.

Moreover, if it is found at step S123 that the predetermined amount of a buffy coat has been collected into the buffy coat collection bag 27, that is, if the first fluid feeder pump 11 has been rotated by the required number of rotations, the control unit 13 blocks all the channel open/close means 81 to 87, inactivates the first fluid feeder pump 11, and terminates the present process [17] (buffy coat collection process (G)).

[18] Thereafter, the blood component collection system 1 executes a process of inactivating the centrifugal separator 20.

In this process, first, the control unit 13 decelerates the centrifugal separator 20 (step S124 in FIG. 5).

Specifically, the rotational frequency of the centrifugal separator drive 10 is decreased under the control of the control unit 13. The rotor 142 is thus decelerated.

Furthermore, the control unit 13 inactivates the centrifugal separator 20 (step S125 in FIG. 5).

Specifically, the rotation of the centrifugal separator drive 10 is stopped in order to inactivate the rotor 142 under the control of the control unit 13.

[19] Thereafter, the blood component collection system 1 executes a blood return process. In the blood return process, the blood components in the blood reservoir space 146 of the rotor 142 are returned.

In the blood return process, the control unit 13 executes blood return (step S126 in FIG. 5).

Specifically, the first channel open/close means 81 is unblocked under the control of the control unit 13. Moreover, the first fluid feeder pump 11 is activated (rotated reversely) at a predetermined rotating speed (preferably, from about 20 mL/min to about 120 mL/min, for example, 90 mL/min).

Consequently, the blood components (mainly red blood cells) remaining in the blood reservoir space 146 of the rotor 142 are released from the outlet 144 of the centrifugal separator 20, and returned (restored) to the donor by way of the first line 21.

Incidentally, the full amount of the blood components (amount of returned blood) is calculated based on the amount of collected blood, the collected amount of plasma, and the collected amount of platelet concentrate.

The first fluid feeder pump 11 is rotated by the number of rotations required to restore the full amount of blood components (amount of returned blood) to the donor under the control of the control unit 13. Thereafter, the first channel open/close means 81 is blocked, the first fluid feeder pump 11 is inactivated, and the present process [19] (blood return process) is terminated.

Thus, the first cycle of platelet collection is completed.

Figure 6:
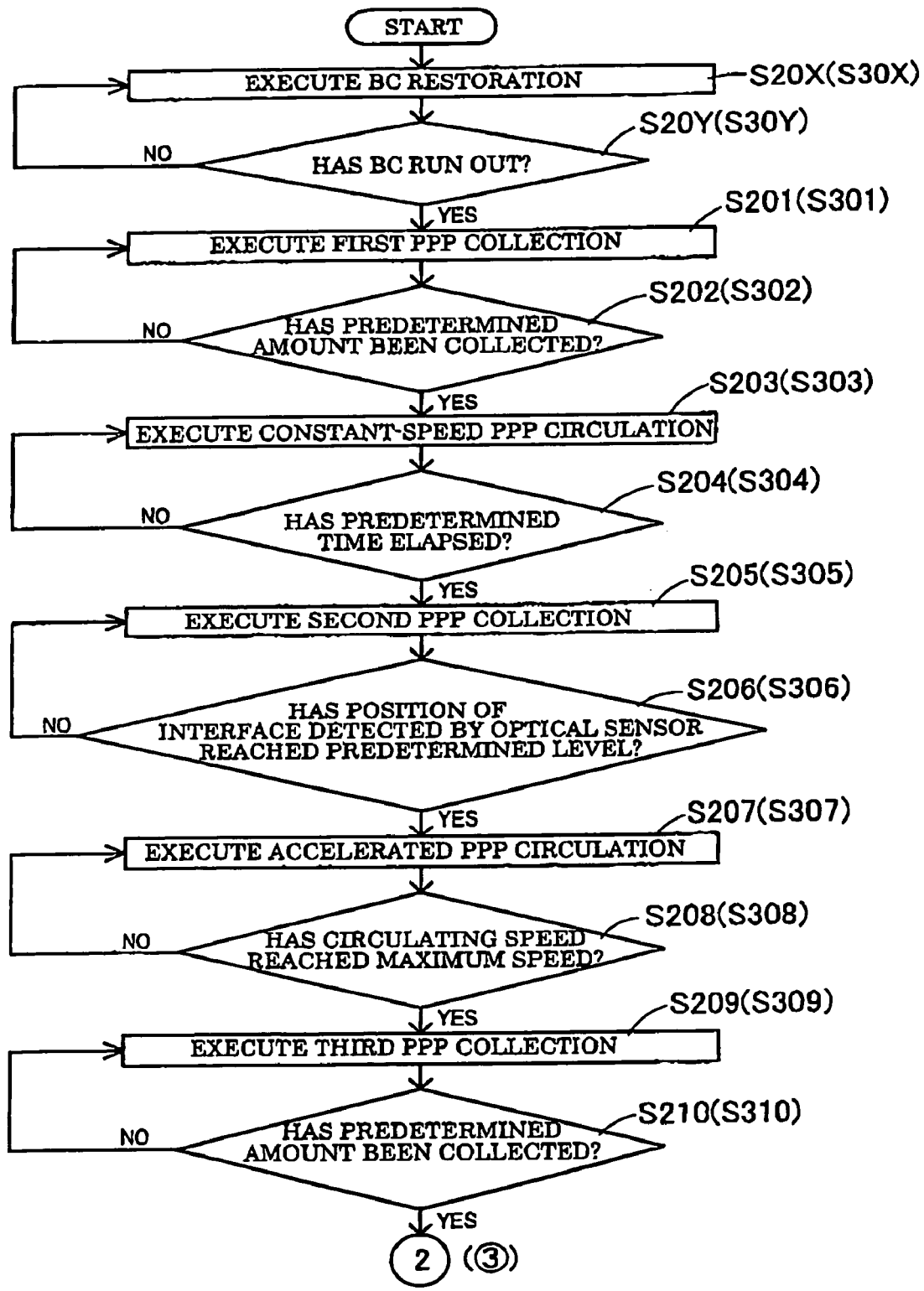
FIG. 6 is a flowchart describing the operation of the blood component collection system according to the present invention.

[2] Second cycle of platelet collection (see FIG. 6 and FIG. 5)

Thereafter, the second cycle of platelet collection is executed.

The second cycle of platelet collection comprises the same processes as the first cycle of platelet collection except that a buffy coat restoration process precedes the first plasma collection process.

[20] First, the blood component collection system 1 executes the buffy coat (BC) restoration process. In the buffy coat restoration process, a collected buffy coat is restored to the blood reservoir space 146 of the rotor 142.

In the buffy coat restoration process, first, the control unit 13 executes buffy coat restoration (step S20X in FIG. 6).

Specifically, the fourth channel open/close means 84 and sixth channel open/close means 86 are unblocked under the control of the control unit 13. The other channel open/close means are left blocked. In this state, the first fluid feeder pump 11 is activated (rotated forward) at a predetermined rotating speed (preferably, from about 60 mL/min to about 250 mL/min, for example, 100 mL/min). Moreover, the centrifugal separator drive 10 is activated at a predetermined rotational frequency (for example, 4800 rpm).

Consequently, the buffy coat in the buffy coat collection bag 27 is fed to the pipe 141 through the inlet 143 of the centrifugal separator 20 by way of the fourth tube 27a and first line 21, and routed to the blood reservoir space 146 of the rotor 142. At this time, the air in the centrifugal separator 20 is fed to the temporary reservoir bag 26' through the second line 22.

Thereafter, the control unit 13 judges whether the buffy coat collection bag 27 has run out of a buffy coat to be restored (step S20Y in FIG. 6).

Specifically, the control unit 13 determines the number of rotations, by which the first fluid feeder pump 11 should be rotated, on the basis of the collected amount of a buffy coat. The control unit 13 then judges whether the first fluid feeder pump 11 has rotated by the number of rotations required to restore the buffy coat.

If it is found at step S20Y that the buffy coat to be restored is left, that is, if the first fluid feeder pump 11 has not rotated by the required number of rotations, the control unit 13 returns to step S20X and repeats the step S20X and subsequent steps.

If it is found at step S20Y that the buffy coat to be restored has run out, that is, the first fluid feeder pump 11 has rotated by the required number of rotations, the control unit 13 terminates the present process [20] (buffy coat restoration process) and proceeds to the first plasma collection process.

[21] to [29] The same processes as the processes [11] to [19] are executed.

Consequently, the second cycle of platelet collection is completed.

Figure 7:
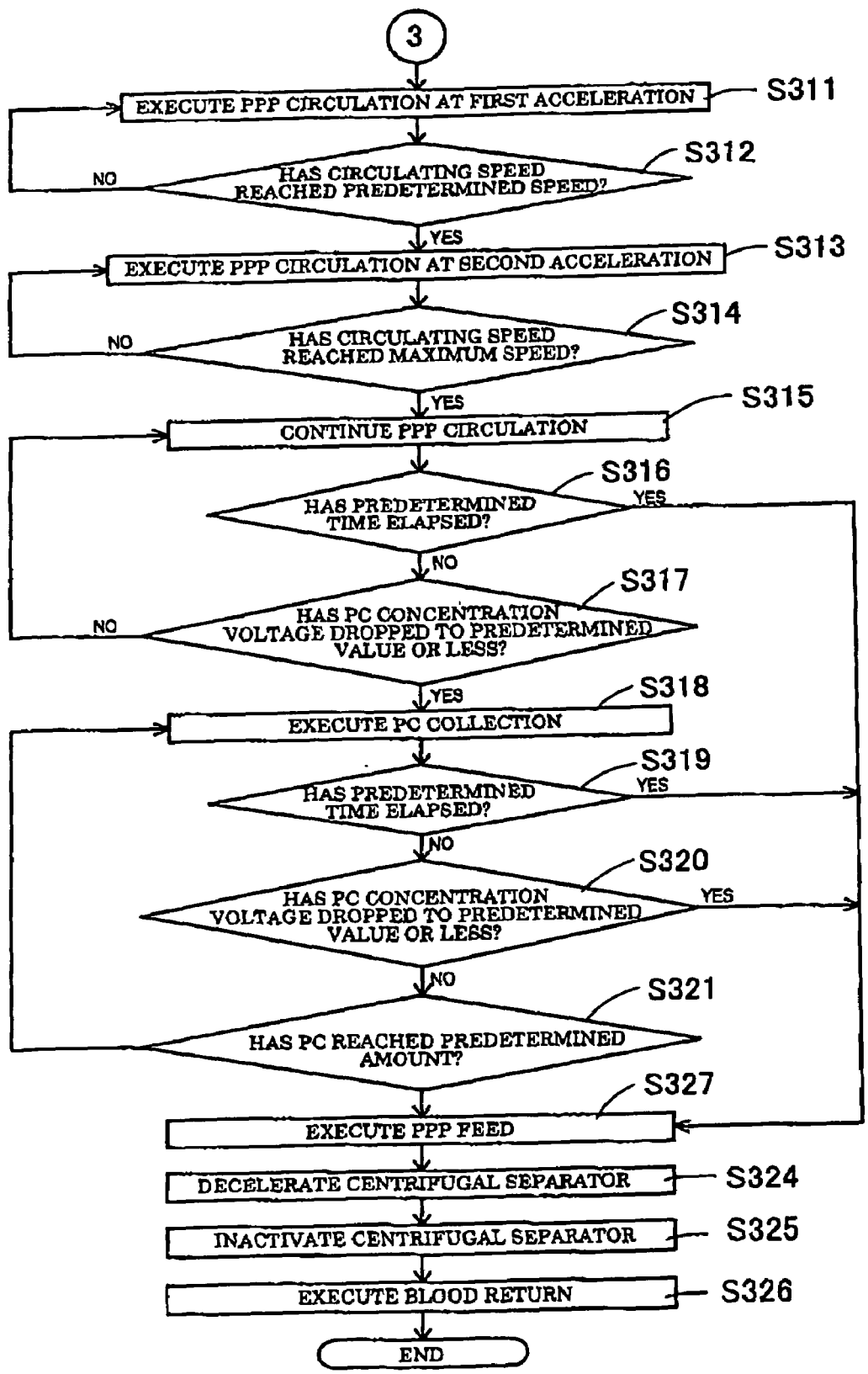
FIG. 7 is a flowchart describing the operation of the blood component collection system according to the present invention.
Figure 8:
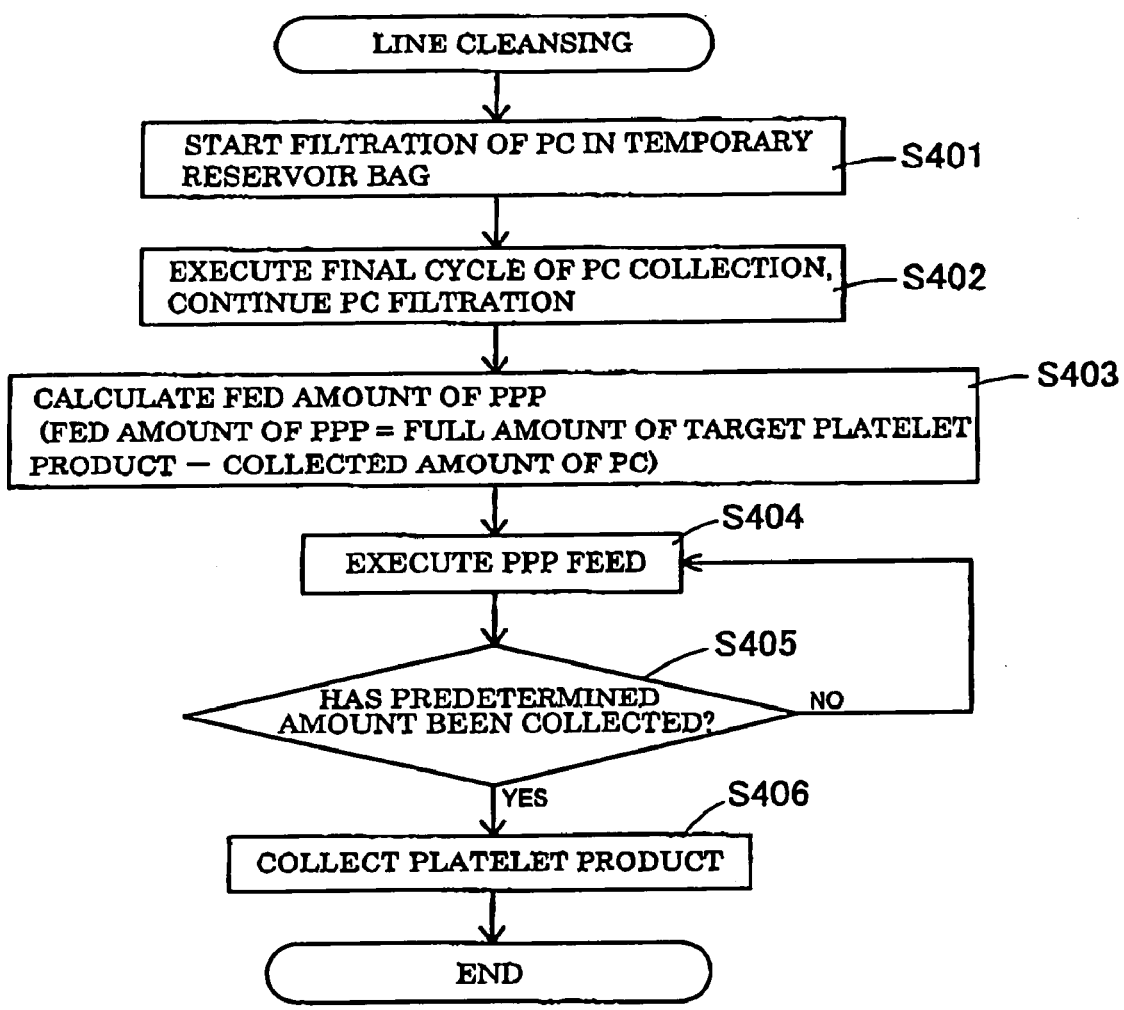
FIG. 8 is a flowchart describing actions to be performed for cleansing a line in the blood component collection system according to the present invention.

[3] Third (final) cycle of platelet collection (see FIG. 6 and FIG. 7)

Successively, the third cycle of platelet collection is executed.

In the third cycle of platelet collection, the same processes as those included in the second cycle of platelet collection are executed except that the buffy coat collection process is not executed and that a line cleansing process is executed for cleansing the platelet collection branch line with plasma.

[30] to [32] The same processes as the processes [20] to [22] are executed.

[33] The same process as the process [23] is executed.

Nearly concurrently with the process [33] (second plasma collection process), the control unit 13 feeds platelet concentrate, which is collected (reserved) temporarily in the temporary reservoir bag 26', to the leukoreduction filter 261. Thus, the platelet concentrate is filtered, that is, leukocyte contained in the platelet concentrate are separated or reduced.

Specifically, the seventh channel open/close means 87 is unblocked under the control of the control unit 13. Consequently, the platelet concentrate in the temporary reservoir bag 26' passes through the tube 262a, leukoreduction filter 261, and tube 263a owing to a fall (own weight). The platelet concentrate is thus carried to the platelet collection bag 26. At this time, the platelet concentrate almost entirely passes through the filtration member of the leukoreduction filter 261. However, the filtration member catches leukocyte. Consequently, the leukocyte contained in a platelet product are highly efficiently reduced.

In order to carry platelet concentrate from the temporary reservoir bag 26' to the platelet collection bag 26, a pump may be employed.

Moreover, instead of the means to be activated under the control of the control unit 13, the seventh channel open/close means 87 may be a clamp capable of manually opening or closing the middle of a channel of the tube 262a.

[34] and [35] The same processes as the processes [24] and [25] are executed.

[36] The same process as the process [26] is executed.

In the present process [36], the platelet concentrate collected into the temporary reservoir bag 26' is fed to the leukoreduction filter 261 and filtered.

[3A] Thereafter, the blood component collection system 1 executes a line cleansing process. In the line cleansing process, plasma is fed from the plasma collection bag 25 to the platelet collection branch line, and the platelet collection branch line is cleansed.

The line cleansing process that is a constituent feature of the present invention will be described with reference to the flowchart of FIG. 8. First, under the control of the control unit 13, the blood component collection system 1 feeds platelet concentrate, which is temporarily collected (reserved) in the temporary reservoir bag 26', to the leukoreduction filter 261, and then executes filtration for separating or reducing leukocyte from the platelet concentrate (S401). The filtration is started substantially concurrently with the start of the second plasma collection process in the final cycle of platelet collection. Thus, the binding time during which a donor is bound is shortened.

The filtration is carried out according to a procedure described below. Specifically, the seventh channel open/close means 87 is unblocked under the control of the control unit 13. This causes the platelet concentrate in the temporary reservoir bag 26' to pass through the tube 262a, leukoreduction filter 261, and tube 263a due to a fall (own weight). The platelet concentrate is thus carried to the platelet collection bag 26. At this time, the platelet concentrate almost entirely passes through the filtration member of the leukoreduction filter 261. However, the filtration member catches leukocyte. Thus, the leukocyte contained in the platelet concentrate are separated or reduced. Eventually, the leukocyte mixed in the platelet product are minimized.

Nearly concurrently with the filtration, the second plasma collection process included in the final cycle of platelet collection is started (S402). At this time, the seventh channel open/close means 87 located downstream the temporary reservoir bag 26' is unblocked. Consequently, platelet concentrate collected in the second plasma collection process in the final cycle is fed to the leukoreduction filter 261 and filtered.

Thereafter, the control unit 13 calculates a fed amount of plasma (PPP) according to an expression below (S403).

Fed amount of plasma=Full amount of a target platelet product−Collected amount of platelet concentrate (PC)

Herein, the full amount of a target platelet product is normally determined prior to blood collection and depends on the specification and unit adopted for a platelet product. Moreover, the collected amount of platelet concentrate (PC) depends on the total number of rotations by which the first fluid feeder pump 11 is rotated with the fourth channel open/close means 84 unblocked.

After the control unit 13 calculates the fed amount of plasma, the control unit 13 feeds plasma to the platelet collection branch line (executes plasma feed) (S404, step S327 in FIG. 7). Specifically, while the second channel open/close means 82 and fourth channel open/close means 84 are left unblocked, the rotating speed of the first fluid feeder pump 11 and the rotational frequency of the rotor 142 are changed under the control of the control unit 13.

The rotating speed of the first fluid feeder pump 11 is, preferably, about 250 mL/min or less, or more preferably, ranges from about 40 mL/min to about 250 mL/min.

Moreover, the rotational frequency of the rotor 142 is set to be larger than the rotational frequency of the rotor 142 adopted in the processes [30] to [36] by, for example, a value ranging from about 300 rpm to about 800 rpm. Preferably, the rotational frequency ranges.from about 5000 rpm to about 5500 rpm.

Consequently, the plasma in the plasma collection bag 25 is routed (fed) to the platelet collection bag 26 by way of the first tube 25*a*, first line 21, rotor 142 (centrifugal separator 20), second line 22, and tube 261*a*. That is, the plasma is routed (fed) from the upstream of the temporary reservoir bag (first container) 26' through the temporary reservoir bag 26', tube 262*a*, leukoreduction filter 261, and tube 263*a* to the platelet collection bag 26.

At this time, the platelets (platelet concentrate having leukocyte separated or reduced) remaining in the leukoreduction filter 261 and the channel defined by the tube 263*a* are collected together with the plasma into the platelet collection bag 26. This results in a high yield of platelets in a platelet product.

Moreover, since plasma is fed from the upstream of the temporary reservoir bag 26', the plasma is routed together with the platelet concentrate (first blood component), which remains in the temporary reservoir bag 26' and the channel of the tube 262*a*, to the leukoreduction filter 261. The yield of platelets in a platelet product can be improved.

As mentioned above, in the cleansing process, the full amount of a platelet product (a blood component in the platelet collection bag 26) is adjusted based on a fed amount of plasma. Consequently, another process for adjusting the full amount of a platelet product can be omitted. Moreover, since the adjustment can be performed in the blood component collection circuit 2 (closed state), a sterile state can be maintained.

The fed amount of plasma ranges, preferably, from about 5 mL to about 200 mL, or more preferably, from about 12 mL to about 150 mL.

The fed amount of plasma is detected as a change (decrease) in the weight of the plasma collection bag 25 by the weight sensor 16.

The control unit 13 then judges from the detection signal sent from the weight sensor 16 whether plasma has been fed to the temporary reservoir bag 26' by the fed (set) amount calculated at step S403 (S405). At this time, if the amount of plasma has not reached the set amount (S405: No), plasma is kept fed (S404). If the amount of plasma has reached the set amount (S405: Yes), the control unit 13 extends control to block the channel open/close means 81 to 84 and 86 and to inactivate the first fluid feeder pump 11. Thereafter, a platelet product is collected (S406). The present process [3A] (line cleansing process) is then terminated.

Prior to the present process [3A], the control unit 13 may extend control to suspend the first fluid feeder pump 11 with the rotor 142 kept rotated. Consequently, in the process [36] (platelet collection process), the buffy coat layer 132 and the layer of red blood cells 133 which are diffused in the blood reservoir space 146 of the rotor 142 (whose thicknesses are increased) can be compressed (the thicknesses can be decreased). Therefore, in the process [3A] (line cleansing process), the buffy coat or red blood cells can be reliably prevented from being mixed in plasma flowing out of the outlet 144 of the rotor 142.

Moreover, the process [3A] may be started after the completion of release of platelet concentrate from the temporary reservoir bag 26'. This can be realized by disposing a bubble sensor or the like, which can detect the presence of bubbles in a channel, in the tube 262*a* near the temporary reservoir bag 26'. [38] and [39] The same processes as the processes [28] and [29] are executed. Incidentally, the same process as the process [27] is omitted.

Consequently, the third cycle of platelet collection is completed.

The number of times by which platelet collection is performed is not limited to three. If necessary, the platelet collection may be performed twice or four or more times.

In the foregoing blood component collection system 1, the leukoreduction filter 261 is used to separate or reduce leukocyte from platelet concentrate separated or collected from blood. Therefore, a platelet product having the least number of leukocyte mixed therein can be prepared.

Moreover, platelets remaining in the leukoreduction filter 261 and tube 263*a* are washed away with plasma and collected into the platelet collection bag 26. Consequently, a platelet product containing platelets at a very high yield can be prepared.

Moreover, platelets are collected (washed away) using plasma (blood component). Therefore, compared with when physiological saline or an anticoagulant is employed, a higher-quality platelet product can be prepared.

Moreover, the configuration of the blood component collection circuit 2 included in the blood component collection system 1 can be determined appropriately but not limited to the illustrated one.

For example, a tube (line) linking the plasma collection bag 25 and platelet collection branch line may be included. In this case, a method for feeding (carrying) plasma from the plasma collection bag 25 to the platelet collection branch line may be a method utilizing a fall or a method employing a pump. Even in this case, the plasma collection bag 25 is, preferably, disposed upstream the temporary reservoir bag 26'.

Moreover, for example, a second plasma collection bag different from the plasma collection bag 25 may be included. Plasma to be fed to the platelet collection branch line during the line cleansing process may be reserved in the second plasma collection bag.

Furthermore, in the blood component collection system 1, conditions can be set for each of processes constituting platelet collection (blood component collection). Moreover, if necessary, any process can be added or omitted.

The blood component collection system according to the present invention has been described in conjunction with the illustrated embodiment. The present invention is not limited to the embodiment. The components of the blood component collection system may be replaced with others that can exhibit the same abilities.

For example, the present invention is not limited to the illustrated optical sensor. Alternatively, for example, a line sensor will do.

The blood component collection system of the present invention is not limited to a case where a platelet product is prepared. Alternatively, for example, the blood component collection system may be adapted to a case where a plasma product, an albumin product, a red blood cell product, or the like is prepared. Moreover, a kind of cells to be separated or reduced using the cell separating filter is not limited to leukocyte.

Next, a concrete example of the present invention will be described.

EXAMPLE

A blood component collection circuit (Terumo Leukoreductive Apheresis set (with a leukoreduction filter) manufactured by Terumo Corp.), and a blood component collection system (Terumo Apheresis machine AC-550 manufactured by Terumo Corp.) were remodeled in order to construct the blood component collection system shown in FIG. 1. The system was used to perform platelet collection (four times) by executing the aforesaid processes.

Moreover, the conditions for each of the processes to be executed in order to achieve platelet collection will be listed below. The interface between blood components to be detected was the interface between a layer of plasma and a buffy coat layer.

[First Plasma Collection Process]
  Rotor: rotational frequency: 4800 rpm
  First fluid feeder pump: rotating speed: 60 mL/min
  Condition for terminating the process:
    A collected amount should reach 30 g.

[Constant-speed Plasma Circulation Process]
  Rotor: rotational frequency: 4800 rpm
  First fluid feeder pump: rotating speed: 200 mL/min
  Condition for terminating the process: 30 sec should elapse.

[Second Plasma Collection Process]
  Rotor: rotational frequency: 4800 rpm
  First fluid feeder pump: rotating speed: 60 mL/min
  Condition for terminating the process:
    The output voltage of the first optical sensor should become 1.8 V.

[Accelerated Plasma Circulation Process]
  Rotor: rotational frequency: 4800 rpm
  First fluid feeder pump: rotating speed: 60 mL/min (initial speed),
    5.0 mL/min/sec (acceleration)
  Condition for terminating the process:
    The rotating speed of the first fluid feeder pump should be 170 mL/min.

[Third Plasma Collection Process]
  Rotor: rotational frequency: 4800 rpm
  First fluid feeder pump: rotating speed: 60 mL/min
  Condition for terminating the process:
    A collected amount should reach 10 g.

[Platelet Collection Process]
  Rotor: rotational frequency: 4800 rpm
  First fluid feeder pump: rotating speed:
    60 mL/min (initial speed),
    2 mL/min/sec (first acceleration)
    When the rotating speed becomes 150 mL/min, the acceleration is changed.
    10 mL/min/sec (second acceleration)
    200 mL/min (maximum speed)
  Condition for terminating the process:
    A collected amount of platelet concentrate should reach 50 mL.

[Buffy Coat Collection Process]
  Rotor: rotational frequency: 4600 rpm
  First fluid feeder pump: rotating speed: 205 mL/min
  Condition for terminating the process:
    A calculated amount of a buffy coat should have been collected

[Blood Return Process]
  First fluid feeder pump: rotating speed: 90 mL/min
  Condition for terminating the process:
    A calculated amount of blood to be returned should have been returned.

[Buffy Coat Restoration Process]
  Rotor: rotational frequency: 4800 rpm
  First fluid feeder pump: rotating speed: 100 mL/min
  Condition for terminating the process:
    A calculated amount of a buffy coat should have been restored.

[Line Cleansing Process]
  Rotor: rotational frequency: 5200 rpm
  First fluid feeder pump: rotating speed: 60 mL/min
  Condition for terminating the process:
    15 mL of plasma should have been fed.

COMPARATIVE EXAMPLE

A blood component collection circuit (Terumo Leukoreductive Apheresis set (with a leukoreduction filter) manufactured by Terumo Corp.) and a blood component collection system (Terumo Apheresis machine AC-560 manufactured by Terumo Corp.) were remodeled in order to construct the blood component collection system shown in FIG. 1. Using the system, platelet collection was performed (four times) in the same manner as in the above example except that the line cleansing process was omitted.

Incidentally, the platelet collection in the comparative example was performed on the same donor as the one in the example and was executed two weeks after the platelet collection.

(Evaluation)

In both the example and comparative example, the collected amount of platelet concentrate in the temporary reservoir bag and the collected amount of a platelet product in the platelet collection bag were measured.

Moreover, the platelet concentrate in the temporary reservoir bag and the platelet product in the platelet collection bag were sampled in order to measure the number of contained platelets and the number of contained leukocyte. For the measurement, a cytometer (Sysmex® SE-9000 manufactured by Sysmex Corp.) was employed. The lower limit of the number of leukocyte measurable by the Sysmex SE-9000 is calculated as $0.1 \times 10^2$ cells/μL. The number of leukocyte contained in a sample and falling below the lower limit is measured according to a Nageotte [1:9] method.

The results of the measurement are listed in Table 1.

TABLE 1

|  |  | In temporary reservoir bag (platelet concentrate) | In platelet collection bag (platelet product) | Yield (%) |
|---|---|---|---|---|
| Example | collected amount [ml] | 200 | 200 | 96.35 |
|  | the number of platelets [cells/bag] | $2.19 \times 10^{11}$ | $2.11 \times 10^{11}$ |  |

TABLE 1-continued

|  |  | In temporary reservoir bag (platelet concentrate) | In platelet collection bag (platelet product) | Yield (%) |
|---|---|---|---|---|
| Comparative Ex. | the number of leukocyte [cells/bag] | $3.0 \times 10^7$ | $1.0 \times 10^4$ | |
| | collected amount [ml] | 200 | 200 | 92.37 |
| | the number of platelets [cells/bag] | $2.36 \times 10^{11}$ | $2.18 \times 10^{11}$ | |
| | the number of leukocyte [cells/bag] | $5.6 \times 10^7$ | $1.0 \times 10^4$ | |

As seen from Table 1, since the line cleansing process is included in the example, a loss of platelets occurring over the platelet collection branch line can be reduced more successfully than it can in the comparative example. Consequentially, the yield of platelets in a platelet product can be improved more successfully.

Specifically, the yield of platelets in the example was 96.35%, while the yield of platelets in the comparative example was 92.37%. Thus, the yield of platelets in a platelet product could be improved approximately 4%. Herein, the yield is calculated as follows: the number of platelets in the platelet collection bag/the number of platelets in the temporary reservoir bag×100 (%).

Incidentally, in both the example and comparative example, leukocyte were successfully reduced from a platelet product.

INDUSTRIAL APPLICABILITY

As described so far, in a blood component collection system according to the present invention, a cell separating filter is used to separate or reduce a predetermined kind of cells. In order to prepare a blood product, for example, a platelet product, leukocyte (especially, lymphocytes) can be reduced from the platelet product (blood product) at a high removable rate. The risk of an attack of fever, isoantigen sensitization, virus infection, or the like can be lowered. High safety can be guaranteed.

Moreover, in a blood component collection system according to the present invention, when a blood product, for example, a platelet product is prepared, platelets remaining in a cell separating filer are collected using, for example, plasma (blood component) as a medium. This results in a high yield of platelets in a platelet product. Moreover, since platelets are collected using the blood component, a high-quality platelet product (blood product) can be prepared.

The invention claimed is:

1. A blood component collection method using a blood component collection system comprising:

a blood component collection circuit including: a centrifugal separator including a rotor that has a blood reservoir space therein and further including an inlet and an outlet which communicate with the blood reservoir space, and centrifuging blood introduced through the inlet with the rotation of the rotor, into a plurality of components in the blood reservoir space; a first container for temporarily reserving therein a first blood component; a cell separating filter for separating or reducing a predetermined kind of cells from the first blood component; and a second container for reserving the first blood component having passed through the cell separating filter, channel open/close means for opening or closing a channel linking the first container and the cell separating filter;

a centrifugal separator driving unit for rotating the rotor of the centrifugal separator; and control means for controlling action of the channel open/close means and the centrifugal separator driving unit; the method comprising steps of:

(A) activating the centrifugal separator driving unit under control of the control means to rotate the rotor, thereby centrifugally separating the blood in the blood reservoir space into a plurality of blood components and collecting the separated first blood component from the centrifugal separator into the first container;

(B) carrying the first blood component in the first container to the second container through the channel linking the first container and the cell separating filter and through the cell separating filter while the channel open/close means is opened under control of the control means;

(C) supplying a second blood component through the first container, the channel linking the first container and the cell separating filter and through the cell separating filter into the second container; and collecting the first blood component, from which the predetermined kind of cells remaining in the cell separating filter have been separated or reduced, together with the second blood component into the second container, wherein the step (C) further includes adjusting a full amount of a blood component to be collected into the second container according to a fed amount of the second blood component.

2. The blood component collection method according to claim 1, wherein the step (C) further includes determining the fed amount of the second blood component based on a difference between a target full amount of the blood component to be collected into the second container and an amount of the first blood component to be carried to the second container.

3. The blood component collection method according to claim 1, wherein the blood component collection circuit further includes a third container for reserving the second blood component, the method further comprising the step of:

(D) activating the centrifugal separator driving unit under control of the control means to rotate the rotor, thereby centrifugally separating the blood in the blood reservoir space into a plurality of blood components and collecting the separated second blood component from the centrifugal separator into the third container, the step (D) being started before execution of the step (B), and the step (C) further includes supplying the second blood component from the third container.

4. The blood component collection method according to claim 3, wherein the step (C) further includes carrying the second blood component from the third container to the first container and then feeding the second blood component together with the first blood component which remains in the first container, to the cell separating filter.

5. The blood component collection method according to claim 4, wherein the blood component collection system further includes channel open/close means for opening or closing a channel linking the first container and the third container, and the step (C) further includes opening the channel open/close means for opening or closing the channel linking the first container and the third container, under control of the control means, to feed the second blood component from the third container to the first container.

6. The blood component collection method according to claim 3, wherein the blood component collection system further includes channel open/close means for opening or closing a channel linking the first container and the outlet of the centrifugal separator, a third container for reserving the second blood component, and includes channel open/close means for opening or closing a channel linking the third container and the outlet of the centrifugal separator;

wherein the step (A) includes collecting the first blood component from the centrifugal separator to the first container while the channel open/close means for opening or closing the channel linking the first container and the outlet of the centrifugal separator is opened under the control of the control means; and the step (D) includes collecting the second blood component from the centrifugal separator to the third container while the channel open/close means for opening or closing the channel linking the third container and the outlet of the centrifugal separator is opened under the control of the control means.

7. The blood component collection method according to claim 6, wherein the step (A) is executed in two or more cycles, and the step (B) is executed at substantially the same time with a last cycle of the step (A).

8. The blood component collection method according to claim 3, wherein the blood component collection circuit further includes a blood collection needle, a first line linking the blood collection needle and the inlet of the centrifugal separator, a second line joined to the outlet of the centrifugal separator, and a fluid feeder pump placed in the first line, wherein the first container is connected to the second line;

the third container is connected to the first line and the second line;

the blood component collection system further includes a feeder pump placed in the first line, the control means further controls activation of the feeder pump, and the step (D) further includes feeding blood collected from a donor to the blood reservoir space of the centrifugal separator through the first line by activation of the fluid feeder pump by the control means, thereby collecting the second blood component having been separated by the centrifugal separator, from the centrifugal separator to the third container.

9. The blood component collection method according to claim 3, wherein the step (D) is started before execution of the step (A).

10. The blood component collection method according to claim 3, wherein the steps (D) and (A) are executed in two or more cycles, and the step (B) is executed at substantially the same time with a last cycle of the step (A).

11. The blood component collection method according to claim 1, wherein the first blood component is plasma containing platelets.

12. The blood component collection method according to claim 1, wherein the second blood component is plasma.

13. The blood component collection method according to claim 1, wherein the cell separating filter is a leukoreduction filter.

14. A blood component collection method using a blood component collection system comprising:

a blood component collection circuit including a centrifugal separator including a rotor that has a blood reservoir space therein and further including an inlet and an outlet which communicate with the blood reservoir space, and centrifuging blood introduced through the inlet by rotation of the rotor, into a plurality of components in the blood reservoir space; a first container for temporarily reserving therein a first blood component; a cell separating filter connected to the first container through a feed tube, and used to separate or reduce a predetermined kind of cells from the first blood component fed through the feed tube; and a second container which is connected to the cell separating filter through a release tube and used for reserving therein the first blood component having passed through the cell separating filter, channel open/close means for opening or closing a channel of the feed tube;

a centrifugal separator driving unit for rotating the rotor of the centrifugal separator; and control means for controlling action of the channel open/close means and the centrifugal separator driving unit;

the method comprising steps of:

(A) activating the centrifugal separator driving unit under control of the control means to rotate the rotor, thereby centrifugally separating the blood in the blood reservoir space into a plurality of blood components and collecting the separated first blood component from the centrifugal separator into the first container;

(B) carrying the first blood component in the first container to the second container through the feed tube, cell separating filter, and release tube in response to a command sent from the control means, while the channel open/close means is opened under control of the control means;

(C) feeding a second blood component through the first container, the feed tube, the cell separating filter and the release tube into the second container; and collecting the first blood component that remains in the cell separating filter and the channel of the release tube and that has the predetermined cells separated or reduced therefrom together with the second blood component into the second container, wherein the step (C) further includes adjusting a full amount of a blood component to be collected into the second container according to a fed amount of the second blood component.

15. The blood component collection method according to claim 14, wherein the step (C) further includes determining the fed amount of the second blood component based on a difference between a target full amount of the blood component to be collected into the second container and an amount of the first blood component to be carried to the second container.

16. The blood component collection method according to claim 14, wherein the blood component collection circuit further includes a third container for reserving the second blood component, the method further comprising the step of:

(D) activating the centrifugal separator driving unit under control of the control means to rotate the rotor, thereby centrifugally separating the blood in the blood reservoir space into a plurality of blood components and collecting the separated second blood component from the centrifugal separator into the third container, the step (D) being started before execution of the step (B), and the step (C) further includes feeding the second blood component from the third container.

17. The blood component collection method according to claim 16, wherein the step (C) further includes carrying the second blood component from the third container to the first container and then feeding the second blood component together with the first blood component which remains in the first container, to the cell separating filter through the feed tube.

18. The blood component collection method according to claim 14, wherein the first blood component is plasma containing platelets.

19. The blood component collection method according to claim 14, wherein the second blood component is plasma.

20. The blood component collection method according to claim 14, wherein the cell separating filter is a leukoreduction filter.

* * * * *